(12) United States Patent
Hamilton et al.

(10) Patent No.: US 7,960,365 B2
(45) Date of Patent: Jun. 14, 2011

(54) COMPOUNDS WITH MEDICINAL EFFECTS DUE TO INTERACTION WITH THE GLUCOCORTICOID RECEPTOR

(75) Inventors: Niall Morton Hamilton, Newhouse (GB); Simon James Anthony Grove, Newhouse (GB); Michael John Kiczun, Newhouse (GB); John Richard Morphy, Newhouse (GB); Brad Sherborne, Newhouse (GB); Peter Thomas Albert Littlewood, Newhouse (GB); Angus Richard Brown, Newhouse (GB); Celia Kingsbury, Cream Ridge, NJ (US); Michael Ohhlmeyer, Plainsboro, NJ (US); Koc-Kan Ho, West Windsor, NJ (US); Steven G. Kultgen, Dayton, NJ (US)

(73) Assignee: N.V. Organon, Oss (NL)

(*) Notice: Subject to any disclaimer, the term of this patent is extended or adjusted under 35 U.S.C. 154(b) by 0 days.

(21) Appl. No.: 11/641,524

(22) Filed: Dec. 19, 2006

(65) Prior Publication Data
US 2007/0149577 A1 Jun. 28, 2007

(51) Int. Cl.
*C07D 401/00* (2006.01)
*A01N 57/00* (2006.01)
(52) U.S. Cl. ................. 514/89; 546/276.1
(58) Field of Classification Search ............. None
See application file for complete search history.

(56) References Cited

FOREIGN PATENT DOCUMENTS

| WO | WO 96/36595 A1 | 11/1996 |
|---|---|---|
| WO | WO 2004/019935 A1 | 3/2004 |
| WO | WO 2006/009876 A2 | 1/2006 |
| WO | WO 2006/046914 A1 | 5/2006 |

OTHER PUBLICATIONS

Dyke et al., caplus an 1997:51534.*
Ornstein et al., caplus an 2000:746417 (2000).*
Beato, et al., "DNA Regulatory Elements for Steroid Hermones," *J. Steroid Biochem.*, 32, 1989, 737-747.
Ellman, et al., "N-tert-Butanesulfinyl Imines: Versatile Intermediates for the Asymmetric Synthesis of Amines," *Acc. Chem. Res.*, 35, 2002, 984-995.
Miyaura, et al., "Palladium-Catalyzed Cross-Coupling Reactions of Organoboron Compounds," *Chem. Rev.*, 95, 1995, 2457-2483.
Nicolaou, et al., "Palladium-Catalyzed Cross-Coupling Reactions in Total Synthesis," *Angew. Chem. Intl. Edn.*, 44, 2005, 4442-4489.
Database Beilstein, Beilstein Institute for Organic Chemistry, Frankfurt-Main, DE; XP002429082 retrieved from XFIRE Database accession No. 7773424, 1982.
Database Chemcats, Chemical Abstracts Service, Columbus, Ohio, US; XP002429083; Accession No. 2005:1526101.
Database Caplus (Online), Chemical Abstracts Service, Columbus, Ohio, US; Miyazaki, Daichi et al.: "Enantioselective Borodeuteride Reduction of Aldimines Catalyzed by Cobalt Complexes: Preparation of Optically Active Deuterated Primary Amines", XP002429084, retrieved from STN Database accession No. 2003:685332.
Database Chemcats, Chemical Abstracts Service, Columbus, Ohio, US; XP002429085; Accession No. 2006:2959389.
Mac Pherson, L. et al., "Discovery of CGS 27023A, a Non-Peptidic, Potent, and Orally Active Stromelysin Inhibitor That Blocks Cartilage Degradation in Rabbits", J. Med. Chem. 40(16):2525-2532 (1997).
Mac Pherson, L. et al., pp. 1-2, Abstract. DOI: 10.1021/jm960871c; ISSN: 0022-2623; CrossFire Beilstein Database, Elsevier Information Systems GmbH (2007-2008).
Miyazaki, D. et al., "Enantioselective Borodeuteride Reduction of Aldimines Catalyzed by Cobalt Complexes: Preparation of Optically Active Deuterated Primary Amines", *Organic Letters* 5(20):3555-3558 (2003).
International Search Report for PCT/EP2006/069814 dated Apr. 25, 2007; and Written Opinion for PCT/EP2006/069814 dated Apr. 25, 2007.

* cited by examiner

*Primary Examiner* — Sun Jae Y Loewe
(74) *Attorney, Agent, or Firm* — Susan L. Hess; Gerard M. Devlin

(57) ABSTRACT

The invention provides for compounds having the structure according to the formula I Formula I

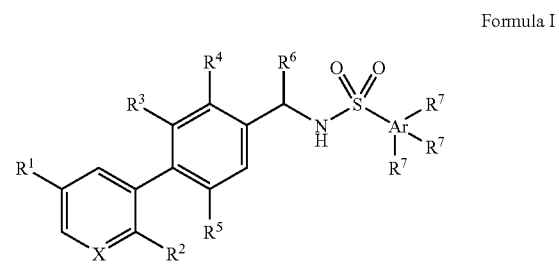

wherein: X is a carbon or nitrogen atom; Ar is phenyl or heteroaromatic ring; $R^1$ is hydrogen, halogen, CN or (1C-4C) alkyl; $R^2$ is hydrogen, halogen or optionally fluorinated (1C-3C)alkoxy; $R^3$ and $R^5$ are independently hydrogen, optionally halogenated (1C-4C)alkyl, optionally halogenated (1C-4C) alkoxy, optionally halogenated aryl(1C-4C)alkoxy, optionally halogenated (1C-4C)alkenyl or hydroxylmethyl; $R^4$ is hydrogen, halogen, optionally halogenated (1C-4C)alkoxy or optionally halogenated aryl(1C-4C)alkoxy; $R^6$ is hydrogen, benzyl, optionally substituted with one or more halogens or (1C-4C)alkyl, or $R^6$ is optionally halogenated (1C-4C)alkyl; each $R^7$ independently is hydrogen, halogen, optionally halogenated (1C-4C)alkyl or optionally halogenated (1C-4C) alkoxy and pharmaceutically suitable acid addition salts thereof for use as glucocorticoid receptor modulators, in particular for treatment of central nervous system disorders.

6 Claims, No Drawings

COMPOUNDS WITH MEDICINAL EFFECTS DUE TO INTERACTION WITH THE GLUCOCORTICOID RECEPTOR

The present invention relates to compounds with glucocorticoid steroid receptor interaction and the use of those compounds for the treatment of stress related disorders, depression and anxiety.

In an organism the glucocorticoid receptor (GR) is involved in a manifold of functions, mostly as a direct consequence of the experience of threatening and/or harmful events. In particular, GR-agonists can be used to modulate immune responses. The GR receptors are also present in the central nervous system, in which tissue it is more difficult to relate their role to specific physiological functions. However, it is reported that antagonists are beneficial in the treatment of depression. Most of the compounds, which are made available for therapeutic interventions targeted on the glucocorticoid receptor are having a steroid skeleton, which makes them harder to prepare than non-steroidal compounds and often less specific for the GR receptor relative to other well-known nuclear receptors, such as the progesterone receptor, the androgen receptor, the mineralocorticoid receptor or the estrogen receptor.

The advantages are that such compounds are easier to prepare and can have less side effects.

Thus, this invention makes compounds available having the structure according to the formula I

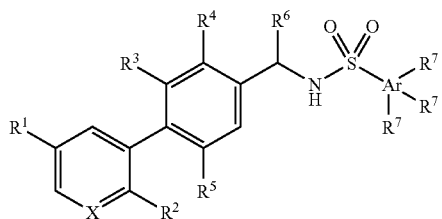

Formula I wherein:
X is a carbon or nitrogen atom;
Ar is benzene or heteroaromatic ring;
$R^1$ is hydrogen, halogen, CN or (1C-4C)alkyl;
$R^2$ is hydrogen, halogen or optionally fluorinated (1C-3C) alkoxy;
$R^3$ and $R^5$ are independently hydrogen, optionally halogenated (1C-4C)alkyl, optionally halogenated (1C-4C)alkoxy, optionally halogenated aryl(1C-4C)alkoxy, optionally halogenated (2C-4C)alkenyl or hydroxylmethyl;
$R^4$ is hydrogen, halogen, optionally halogenated (1C-4C) alkoxy or optionally halogenated aryl(1C-4C)alkoxy;
$R^6$ is hydrogen, benzyl, optionally substituted with one or more halogens or (1C-4C)alkyl, or $R^6$ is optionally halogenated (1C-4C)alkyl;
each $R^7$ independently is hydrogen, halogen, optionally halogenated (1C-4C)alkyl or optionally halogenated (1C-4C) alkoxy;
and pharmaceutically suitable addition salts thereof.

Another embodiment is a compound as defined above but:
Ar is thiazole, thiophene, isoxazole, furan or 1H-pyrazole;
$R^1$ is hydrogen, halogen, CN or methyl, whereby fluor or chlor are preferred halogens;
$R^2$ is hydrogen, halogen or optionally fluorinated (1C-2C) alkoxy, whereby chlor is preferred halogen;
$R^3$ and $R^5$ are independently hydrogen, (1C-3C)alkyl, benzyloxy, (2C-3C)alkenyl, hydroxylmethyl or optionally fluorinated methoxy;
$R^4$ is hydrogen, F, Cl or methoxy and at least one of $R^3$, $R^4$ and $R^5$ is hydrogen;
$R^6$ is hydrogen or methyl;
each $R^7$ independently is hydrogen, optionally fluorinated methyl, optionally fluorinated methoxy, F. Cl, Br, or cyano;
or a pharmaceutically suitable addition salt thereof.

Another more specific embodiment is a compound as defined by formula 1 whereby:
X is a carbon or nitrogen atom;
Ar is benzene or heteroaromatic ring;
$R^1$ is halogen, CN or (1C-4C)alkyl;
$R^2$ is halogen or optionally fluorinated (1C-3C)alkoxy;
$R^3$ and $R^5$ are independently hydrogen, optionally halogenated (1C-4C)alkyl, optionally halogenated (1C-4C)alkoxy, optionally halogenated aryl(1C-4C)alkoxy, optionally halogenated (2C-4C)alkenyl or hydroxylmethyl;
$R^4$ is hydrogen, halogen, optionally halogenated (1C-4C) alkoxy or optionally halogenated aryl(1C-4C)alkoxy;
at least one of $R^3$, $R^4$ or $R^5$ is hydrogen;
$R^6$ is hydrogen or methyl;
each $R^7$ independently is halogen, optionally halogenated (1C-4C)alkyl or optionally halogenated (1C-4C)alkoxy;
or a pharmaceutically suitable addition salt thereof.

Terms used have the following meaning:
The prefixes (1C-3C) or (1C-4C) etc. have the usual meaning to restrict the meaning of the indicated group to those with 1 to 3, 1 to 4 etc. carbon atoms.

Alkyl represents a branched or unbranched alkyl group having 1-6 carbon atoms.

Examples of (1C-6C)alkyl groups include methyl, ethyl, propyl, isopropyl, butyl, and tertiary butyl.

Alkenyl represents a branched or unbranched alkenyl group. Examples of (2C-3C) alkenyl groups include ethenyl, 1-propenyl, and 2-propenyl.

A heteroaromatic ring is a ring structure with a circularly delocalized bonding system and containing at least one of nitrogen, oxygen or sulphur, such as pyridyl, thiazole, thiophene, isoxazole, furan, 1Hpyrazole, thiadiazolyl, thienyl.

Halogenated means that one or more halogen substituents are on the group, for example in $CF_3$, which is a halogenated methyl.

Halogen is fluor, chlor, brom or iodine.

The term pharmaceutically acceptable salt represents those salts which are, in the context of administration of a pharmaceutical formulation to humans or animals, suitable for use in view of safety and absence of irritation, allergic response and the like, and are commensurate with a reasonable benefit/risk ratio. Pharmaceutically acceptable salts are well known in the art. They may be obtained during the final isolation and purification of the compounds of the invention, or separately by reacting the free base function with a suitable mineral acid such as hydrochloric acid, phosphoric acid, or sulfuric acid, or with an organic acid such as for example ascorbic acid, citric acid, tartaric acid, lactic acid, maleic acid, malonic acid, fumaric acid, glycolic acid, succinic acid, propionic acid, acetic acid, methanesulfonic acid, and the like. The acid function can be reacted with an organic or a mineral base, like sodium hydroxide, potassium hydroxide or lithium hydroxide.

Compounds according to the invention can be used in treatments which aim at changing the level of activity of the secondary signal following activation of the glucorticoid receptor, mostly by their interfering action with the natural action of glucocorticoid receptor activation. The nuclear receptor is a modulator of the genome, which modulation is set on or off, or is moderated by the receptor when it is occupied by a compound interacting with the receptor. Such treatments are for depression, anxiety, whereof specifically posttraumatic stress disorder is to be mentioned and diseases having abnormal hypophysio-adrenocortical axis disturbances, reflected for example in high cortisol levels in plasma or diseases where abnormal/dysfunctional GR activity occurs. In view of these uses the invention also relates to the use of a compound according to the invention for the manufacture of a medicament for said treatments and for treatment of said diseases or symptoms. The person skilled in the art will appreciate that this use comprises administering a therapeutically effective amount of a compound according to the invention, optionally in combination with other useful drugs for the diseased to be treated. An amount is understood to be expressed in terms of the number of moles or the weight of the free base component in a pharmaceutical composition.

Methods to determine receptor binding as well as in vitro and in vivo assays to determine biological activity of the compounds are well known. As an in vitro method, a biotechnologically expressed receptor can be contacted with the compound to be tested and binding or stimulation or inhibition of a functional response can be measured. To measure binding, isolated cytosol containing the expressed GR may be used. Radioactive or fluorescence labelled compounds may be used. As reference compound, native hormone or other compounds binding to the receptor can be used. As an alternative, also competition binding assays can be performed. Specificity for the GR receptor can be determined by testing the compound not only for the glucocorticoid receptor, but also for other well-known receptors such as progesterone receptor, androgen receptor, mineralocorticoid receptor and/or estrogen receptor.

For measurement of a functional response in vitro, isolated DNA encoding the glucocorticoid receptor gene, preferably the human receptor, is expressed in suitable host cells. Such a cell might be the Chinese Hamster Ovary (CHO) cell, but other cells are also suitable. Preferably the cells are of mammalian origin.

Methods to construct recombinant glucocorticoid receptor-expressing cell lines are well known in the art. Expression of receptor is attained by expression of the DNA encoding the desired protein. As is well known, expression systems are now available which are compatible with a wide variety of hosts, including prokaryotic hosts such as bacteria and eukaryotic hosts such as yeast, plant cells, insect cells, mammalian cells, avian cells and the like. Cells expressing the receptor are then contacted with the test compound to observe modulation of a functional response.

In addition to direct measurement of mRNA or protein levels in the exposed cells, cells can be used which in addition to transfection with receptor encoding DNA are also transfected with a second DNA encoding a reporter gene the expression of which responds to binding of the receptor towards responsive elements in the promoter of the particular reporter gene. Such responsive elements might be classical hormone responsive elements, well known in the art and described in Beato, M, Chalepakis, G, Schauer, M, Slater, EP (1989) J. Steroid Biochem. 5:737-47 or might be constructed in such a way that they are connected to novel responsive elements. In general, reporter gene expression might be controlled by any response element reacting to glucocorticoid receptor binding. Suitable reporter genes are e.g. LacZ, alkaline phosphatase, firefly luciferase and green fluorescence protein.

Compounds according to the invention can bind to the GR receptor with an affinity of $<10^{-6}$ M. More preferred compounds have binding affinity of $<10^{-7}$ M and even better is $10^{-8}$ M. The skilled person will recognize that desirable $EC_{50}$ values are dependent on the compound tested. However, a compound which has a higher $EC_{50}$ than mentioned above, but is very selective for the GR receptor, may be even a better compound in view of reduced side effects.

Administration of a compound according to the invention will be greatly aided by the manufacture of pharmaceutical compositions. The present invention therefore also relates to a pharmaceutical composition comprising a compound according to the invention mixed with a pharmaceutically acceptable excipient, such as the ones described in Gennaro et al., Remmington: *The Science and Practice of Pharmacy*, $20^{th}$ Edition, Lippincott, Williams and Wilkins; 2000; see especially part 5: pharmaceutical manufacturing. Suitable excipients are made available e.g., in the Handbook of Pharmaceutical Excipients, $2^{nd}$ Edition; Editors A. Wade and P. J. Weller, American Pharmaceutical Association, Washington, The Pharmaceutical Press, London, 1994. The mixtures of a compound according to the present invention and a pharmaceutically acceptable excipient may be compressed into solid dosage units, such as tablets, or be processed into capsules or suppositories. For making dosage units e.g., tablets, the use of conventional additives such as fillers, colorants and polymeric binders is contemplated. In general, any pharmaceutically acceptable additive, which does not interfere with the function of the active compounds, can be used. Suitable fillers with which the pharmaceutical compositions can be prepared and administered include lactose, starch, cellulose and derivatives thereof, or mixtures thereof used in suitable amounts. Commonly the route of administration is by oral intake or as rectal suppository. Other routes of administration of the medicines comprising a compound according to the invention can be for injection into veins, subcutaneously or intra-muscularly.

The methods needed to synthesize the compounds of the present invention are shown in the Schemes below and in the procedures provided in the Examples. In each of the schemes the R groups and X correspond to the substitution pattern noted in the Examples and to Formula I. The compounds of the present invention can be synthesized using techniques known to those skilled in the art.

The compounds of the present invention are prepared via various metal mediated cross coupling methods [Suzuki et. al., *Chem. Rev.*, 95: 2457, (1995) and Nicolaou et. al. *Angew. Chem. Intl. Edn.*, 44 (29), 4442-4489 (2005)] where reagent I (Y=boronic acid, boronate ester, halide, triflate or other compatible coupling partner) and reagent II (Z=halide, triflate, boronic acid, boronate ester or other compatible coupling partner) are coupled to yield biaryl carbonyl containing intermediates III (Scheme 1). The reagents of general structure I and II are either commercially available or easily accessible via synthetic routes which are well documented in the literature.

Scheme 1

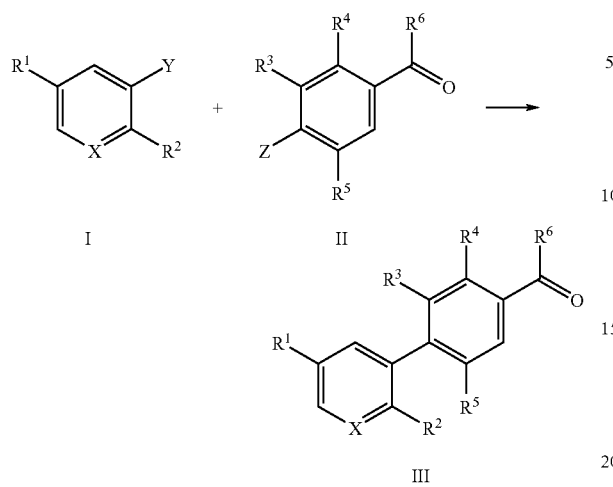

The above mentioned reaction is typically conducted by reacting an appropriate aryl bromo, iodo or triflate compound with an aryl boronic acid derivative in the presence of a palladium catalyst such as tetrakis(triphenylphosphine)palladium (0) and a base in a solvent such as toluene or dimethylformamide.

Intermediate biaryl-carbonyl derivatives III are then converted into biaryl amine derivatives V via intermediate imine derivatives IV, where $R^8$=H, alkyl/aryl sulfinate, oxime ether (Scheme 2). The reagents of general structure III, IV and V are either commercially available or easily accessible via synthetic routes which are well documented in the literature [Ellman et. al., *Acc. Chem. Res.*, 35, 984-995 (2002)].

Scheme 2

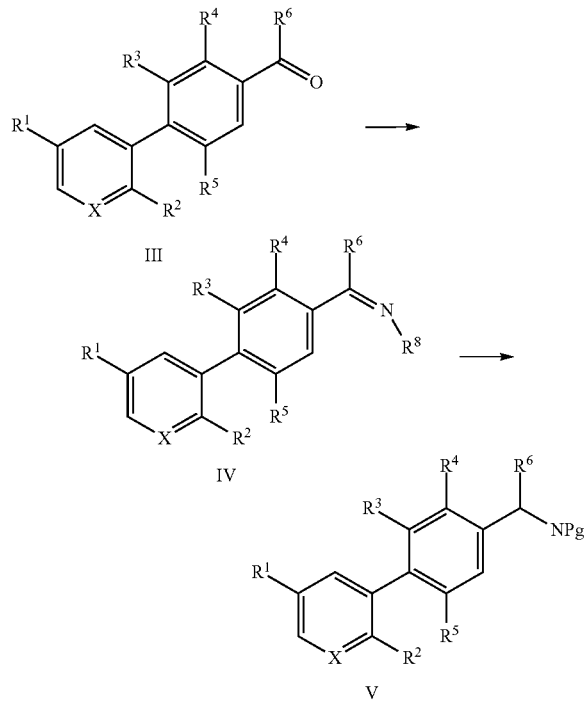

Compounds of general structure V may also be prepared starting with reagents of general structure VI and compatible reagents of general structure I, where Y and Z are as described above (Scheme 3). In general the nitrogen protected derivatives of structure VI where, for example, NPg=NH$_2$, NHBoc, sulphonamide, phthaloyl, N-sulphonylimide are either commercially available or easily accessible via synthetic routes which are well documented in the literature.

Scheme 3

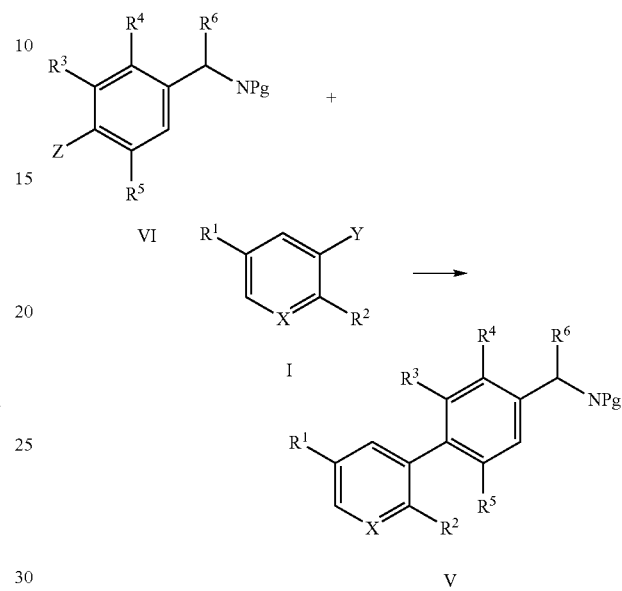

Similar methods can also be used for the asymmetric synthesis of chiral intermediates of type V via, for example, reduction of chiral imine derivatives of type IV where $R^8$=S(O)$^t$Bu (R or S enantiomer) as described by Ellman [Ellman et. al., *Acc. Chem. Res.*, 35, 984-995 (2002)] (Scheme 4).

Scheme 4

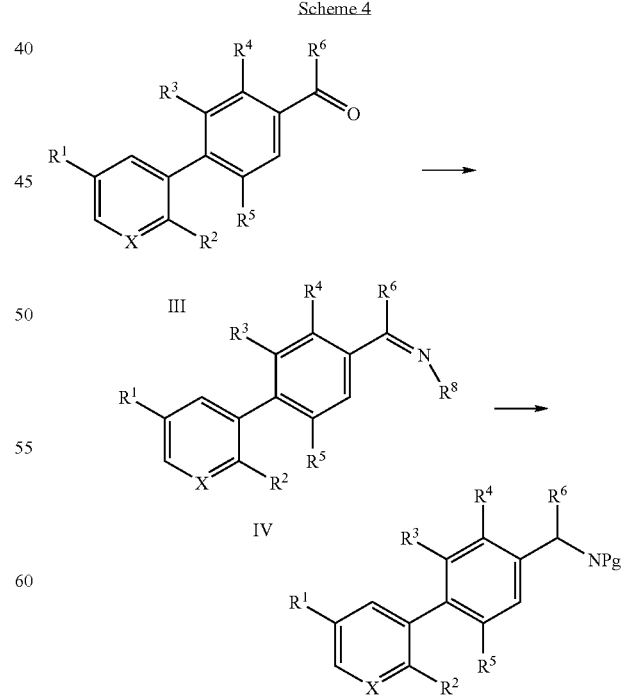

Compounds of general structure V can be converted to the compounds of the present invention with Formula I by reaction with acylating reagents such as sulphonyl chlorides or activated sulphonate esters (Scheme 5). The required sulphonyl chlorides or activated sulphonate ester reagents are either commercially available or easily accessible via synthetic routes which are well documented in the literature.

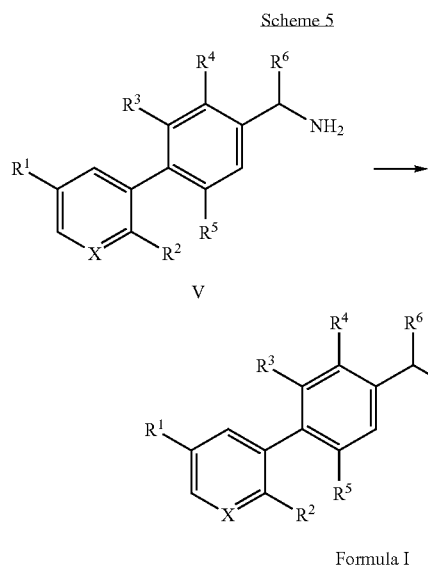

Scheme 5

Formula I

The above mentioned reaction is typically conducted by reaction of an amine V and aryl sulphonyl chloride in a solvent such as dichloromethane and in the presence of an organic base such as triethylamine.

The procedures for synthesizing compounds of the present invention also include steps of analysis and purification employing techniques such as column chromatography, flash chromatography, thin-layer chromatography (TLC), high pressure chromatography (HPLC), distillation and recrystallisation. The compounds can be characterized using techniques well known in the chemical arts, including proton ($^1$H) and carbon-13 ($^{13}$C) nuclear magnetic resonance (NMR) spectroscopy, infrared (IR) and ultraviolet (UV) spectroscopy, elemental analysis, HPLC and mass spectroscopy (LCMS), specific rotation ($[\alpha]_D$), and melting point (mp).

Some compounds of the present invention possess at least one stereogenic carbon atom and may therefore be obtained as pure enantiomer or diastereomer or as a mixture of enantiomers. Methods for preparing pure enantiomers [Ellman et. al., *Acc. Chem. Res.*, 35, 984-995 (2002)] and racemic mixtures are both described in the following examples, as is chiral chromatography of a racemic mixture to give the component enantiomers.

EXAMPLE 1

(R)-5-Chloro-1,3-dimethyl-1H-pyrazole-4-sulfonic acid [1-(5'-chloro-2'-ethoxy-biphenyl-4-yl)-ethyl]-amide A suspension of 5-chloro-2-ethoxyphenylboronic acid (601 mg, 3.0 mmol), palladium (II) acetate (33 mg, 0.15 mmol) and (R)-1-(4-bromophenyl)ethylamine (295 mg, 1.5 mmol) in water (4 ml) was heated for 5 min at 200° C. in a Smithcreator microwave oven. The reaction mixture was diluted with dichloromethane and purified on a Strata™ 5 g/20 ml SCX column (eluted with 2M ammonia in methanol) to give (R)-1-(5'-chloro-2'-ethoxy-biphenyl-4-yl)-ethylamine (341 mg, 1.2 mmol, 82%). To a solution of 1-(5'-chloro-2'-ethoxy-biphenyl-4-yl)-ethylamine (30 mg, 0.1 mmol) in dichloromethane (0.75 ml) was added triethylamine (36 mg, 0.35 mmol) and 5-chloro-1,3-dimethyl-1H-pyrazole-4-sulfonyl chloride (30 mg, 0.13 mmol) in dichloromethane (0.5 ml). The reaction mixture was then agitated at room temperature for 16 h and quenched with acetic acid (200 µl). Purification by preparatory LCMS and removal of solvent under reduced pressure gave the title compound (21 mg, 0.04 mmol, 40%): $^1$H NMR (400 MHz, DMSO-$d_6$): δ 8.25 (d, 1H), 7.32-7.37 (m, 3H), 7.21-7.24 (m, 3H), 7.10 (d, 1H), 4.35 (m, 1H), 4.05 (m, 2H), 2.20 (s, 3H), 1.26-1.35 (m, 6H) ppm; MS (ESI) m/z: value [M+H]$^+$.

EXAMPLE 2

(R)-5-Chloro-1,3-dimethyl-1H-pyrazole-4-sulfonic acid [1-(2'-methoxy-5'-methyl-biphenyl-4-yl)-ethyl]-amide Prepared in a similar manner to (R)-5-chloro-1,3-dimethyl-1H-pyrazole-4-sulfonic acid [1-(5'-chloro-2'-ethoxy-biphenyl-4-yl)-ethyl]-amide (Example 1) using 2-methoxy-5-methylphenylboronic acid and (R)-1-(4-bromophenyl) ethylamine to give (R)-1-(2'-methoxy-5'-methyl-biphenyl-4-yl)-ethylamine which was then reacted with 5-chloro-1,3-dimethyl-1H-pyrazole-4-sulfonyl chloride. Title compound: $^1$H NMR (400 MHz, DMSO-$d_6$): δ 8.25 (d, 1H), 7.27 (d, 2H), 7.20 (d, 2H), 7.12 (d, 1H), 7.02 (s, 1H), 6.97 (d, 1H), 4.35 (q, 1H), 3.72 (s, 3H), 3.55 (s, 3H), 2.28 (s, 3H), 2.20 (s, 3H), 1.33 (d, 3H) ppm; MS (ESI) m/z: value [M+H]$^+$.

EXAMPLE 3

(R)-5-Methyl-2-trifluoromethyl-furan-3-sulfonic acid [1-(2'-trifluoromethoxy-biphenyl-4-yl)-ethyl]-amide A suspension of 2-trifluoromethoxyphenylboronic acid (0.410 g, 2 mmol), palladium (II) acetate (22.4 mg, 10 µmol) and (R)-1-(4-bromophenyl)ethylamine (0.200 g, 1 mmol) in water (4.5 ml) was heated for 5 min at 200° C. in a Smithcreator microwave oven. Methanol (5 ml) was added to the resulting suspension and this was then applied a Strata™ 5 g/20 ml SCX column. The impurities were washed away with methanol (5×20 ml) and the intermediate amine then eluted with 2M ammonia in methanol (2×20 ml). The solvent was removed to give (R)-2'-trifluoromethoxy-biphenyl-4-yl)-ethylamine as an oil. An aliquot of this oil (11.2 mg, 40 µmol) was treated overnight with 5-methyl-2-trifluoromethyl-furan-3-sulfonyl chloride (80 µmol, 2 equivalents) in dichloromethane (1 ml) containing diisopropylethylamine (50 µL). The reaction was then quenched by the addition of acetic acid (500 µL) and the desired product isolated by reverse phase HPLC (ZORBAX SB-C18 PrepHT 21.2×100 mm) eluting with a linear gradient of acetonitrile/water (0.1% TFA). The product-containing fractions were then evaporated to yield the title compound (13.4 mg) as a clear glass: $^1$H NMR (400 MHz, DMSO-$d_6$): δ 8.5 (d, 1H), 7.6-7.4 (m, 4H), 7.3 (s, 4H), 7.1 (s, 1H), 4.5 (m, 1H), 2.33 (s, 3H), 1.38 (d, 3H) ppm; MS (ESI) m/z: 492.1 [M–H]$^-$.

EXAMPLE 4

(R)-1,3,5-Trimethyl-1H-pyrazole-4-sulfonic acid [1-(5'-fluoro-2'-methoxy-biphenyl-4-yl)-ethyl]-amide Palladium acetate (56 mg, 0.25 mmol) was added to a mixture of 5-fluoro-2-methoxyphenylboronic acid (850 mg, 5.0 mmol) and (R)-1-(4-bromophenyl)ethylamine (500 mg, 2.5 mmol) in water (20 ml). This mixture was heated for 5 min at 200° C. in a Smithcreator microwave oven and then diluted with methanol (200 ml). The mixture was purified on a SCX column (20 g) using 2M ammonia in methanol to elute the intermediate amine. Evaporation of solvents under reduced pressure gave (R)-1-(5'-fluoro-2'-methoxy-biphenyl-4-yl)-ethylamine as a gum (580 mg, 2.37 mmol, 96.6%). Triethylamine (41.1 µl, 0.295 mmol) and 1,3,5-trimethyl-1H-pyrazole-4-sulfonyl chloride (20.5 mg, 0.0984 mmol) were added to a solution of (R)-1-(5'-fluoro-2'-methoxy-biphenyl-4-yl)-ethylamine (20 mg, 0.082 mmol) in dichloromethane (1 ml) and the resulting solution shaken at room temperature overnight. The reaction mixture was washed with saturated sodium bicarbonate solution (500 µl), the dichloromethane layer separated, dried over magnesium sulfate and the solvent evaporated. Purification by preparatory LCMS and removal of solvent under reduced pressure gave the title compound (13.8 mg, 0.033 mmol, 40%): $^1$H NMR (400 MHz, CDCl$_3$): δ7.37, 7.14 (a/b, 4H), 7.02-6.87 (m, 3H), 4.68 (m, 1H), 4.48 (t, 1H), 3.78 (s, 3H), 3.55 (s, 3H), 2.35 (s, 3H), 2.22 (s, 3H), 1.50 (d, 3H) ppm; MS (ESI) m/z: 417 [M+H]$^+$.

EXAMPLE 5

(R)-3,4-Difluoro-N-[1-(5'-fluoro-2'-methoxy-biphenyl-4-yl)-ethyl]-benzenesulfonamide A mixture of (R)-1-(4-bromophenyl)ethylamine (0.10 g, 0.5 mmol), 5-fluoro-2-methoxyphenyl boronic acid (0.17 g, 1 mmol), and palladium (II) acetate (0.011 g, 0.05 mmol) was heated for 5 min at 200° C. in a Smithcreator microwave oven. The mixture was then poured onto an SCX column, washed with dichloromethane/methanol, and the intermediate amine eluted using 1M ammonia in methanol (50 ml). Evaporation of solvents under reduced pressure gave (R)-1-(5'-fluoro-2'-methoxy-biphenyl-4-yl)-ethylamine. To a solution of (R)-1-(5'-fluoro-2'-methoxy-biphenyl-4-yl)-ethylamine (0.25 g, 0.1 mmol) in dichloromethane (1 ml) was added triethylamine (0.025 g, 0.25 mmol) and 2,4 difluorophenyl-sulfonyl chloride (0.043 g, 0.2 mmol). The solution was stirred overnight and then quenched with acetic acid (0.5 ml). Purification by preparatory LCMS and removal of solvent under reduced pressure gave the title compound: $^1$H NMR (400 MHz, DMSO): δ 8.58 (d, 1H), 7.64 (q, 1H), 7.30-6.98 (m, 9H), 4.44 (dq, 1H), 3.74 (s, 3H), 1.36 (d, 3H) ppm; MS (ESI) m/z: value [M+H]$^+$.

EXAMPLE 6

N-(5'-Fluoro-2,2'-dimethoxy-biphenyl-4-ylmethyl)-4-methoxy-benzenesulfonamide

To a stirred solution of 4-hydroxy-3-methoxybenzaldehyde (2 g, 14.7 mmol) in dichloromethane (20 ml) was slowly added trifluoromethanesulfonic anhydride (4.5 g, 17.64 mmol) and pyridine (1.5 ml, 14.7 mmol) at 0° C. under nitrogen atmosphere. The solution was stirred for 16 h at ambient temperature, ice-water slurry added and then extracted with dichloromethane. The combined extracts were dried over anhydrous sodium sulfate and the solvent evaporated. The residue was flash chromatographed over silica gel eluting with 4:1 heptane/ethyl acetate and the solvent evaporated to give trifluoromethanesulfonic acid-4-formyl-2-methoxy-phenyl ester (3.5 g) as colourless oil. To a stirred solution of trifluoromethanesulfonic acid-4-formyl-2-methoxy-phenyl ester (3.5 g, 12.3 mmol) in tetrahydrofuran (50 ml) was added 5-fluoro-2-methoxyphenyl boronic acid, lithium chloride (0.05 g, 1.18 mmol), 2M sodium carbonate (14 ml) and tetrakis(triphenylphosphine)palladium (0) (0.22 g, 0.18 mmol). The reaction mixture was refluxed for 5 days then concentrated under reduced pressure. The concentrate was dissolved in ethyl acetate, washed with water, dried over sodium sulfate and the solvent evaporated. The residue was flash chromatographed over silica gel eluting with 5:1 heptane/ethyl acetate and the solvent evaporated to give 5'-fluoro-2,2'-dimethoxy-biphenyl-4-carbaldehyde (2.65 g) as a yellow oil. To a stirred solution of 5'-fluoro-2,2'-dimethoxy-biphenyl-4-carbaldehyde (2.65 g, 9.16 mmol) in pyridine (50 ml) was added methoxyamine hydrochloride (0.474 g, 10.1 mmol) at ambient temperature under nitrogen atmosphere. The reaction mixture was stirred for 16 h. Following evaporation of pyridine under reduced pressure, the residue was dissolved in dichloromethane, washed with water and dried over anhydrous sodium sulfate. Evaporation of solvent followed by purification on a SCX column eluting with methanol gave 5'-fluoro-2,2'-dimethoxy-biphenyl-4-carbaldehyde-O-methyl-oxime (1.05 g) as an oil. A stirred solution of 5'-fluoro-2,2'-dimethoxy-biphenyl-4-carbaldehyde-O-methyl-oxime (0.182 g, 0.63 mmol) and 10% palladium on activated carbon in ethanol (10 ml) and 2M hydrogen chloride (5 drops) was degassed at ambient temperature then purged with hydrogen at atmospheric pressure for 16 h in a sealed vessel. The reaction mixture was then filtered through dicalite and evaporated. The residue was basified to pH 11 with aqueous sodium carbonate, extracted with dichloromethane and dried over anhydrous sodium sulfate. Evaporation of solvent gave C-(5'-fluoro-2,2'-dimethoxy-biphenyl-4-yl)-methylamine (0.27 g) as a gum. To a stirred solution of C-(5'-fluoro-2,2'-dimethoxy-biphenyl-4-yl)-methylamine in dichloromethane (5 ml) was added 4-methoxybenzene sulfonyl chloride (0.03 g, 0.12 mmol) and triethylamine (0.034 ml, 0.24 mmol). The reaction mixture was stirred for 16 h. Water was added and the mixture was filtered through a hydrophobic filter, then flash chromatographed over a SCX column eluting with methanol. Purification by preparatory LCMS and removal of solvent under reduced pressure gave the title compound (0.01 g) as gum: MS (ESI) m/z: 432.3 [M+H]$^+$.

EXAMPLE 7

4-Chloro-N-(2,5'-dimethyl-2'-methoxy-biphenyl-4-ylmethyl)-benzenesulfonamide

Prepared in a similar manner to N-(5'-Fluoro-2,2'-dimethoxy-biphenyl-4-ylmethyl)-4-methoxy-benzenesulfonamide (Example 6) starting with trifluoro-methanesulfonic acid-4-formyl-2-methyl-phenyl ester and 2-methyl-5-methoxyphenyl boronic acid. Title compound: $^1$H NMR (400 MHz, CDCl$_3$): 7.78-7.81 (d, 2H), 7.46-7.48 (d, 2H), 7.10 (d, 1H), 7.15 (d, 1H), 7.00 (d, 2H), 6.87 (s, 1H), 6.85 (d, 2H), 4.65-4.67 (m, 1H), 4.15-4.2 (d, 2H), 3.71 (s, 3H), 2.31 (s, 3H), 2.06 (s, 3H) ppm; MS (ESI) m/z: 438.0 [M+Na]$^+$.

EXAMPLE 8

(R)—N-{1-[4-(2-Ethoxy-pyridin-3-yl)-phenyl]-ethyl}-2-trifluoromethoxy-benzenesulfonamide To a solution of (R)-1-(4-bromophenyl)ethylamine (1.0 g, 5 mmol) in methanol (10 ml) was added sodium hydrogen carbonate (1.26 g, 15.0 mmol) and di-tert-butyl dicarbonate (1.2 g, 5.5 mmol). The reaction mixture was sonicated for 4 h. The solvent was evaporated and the residue partitioned between ethyl acetate and water. The organic phase was washed with brine, dried over anhydrous magnesium sulfate and the solvent removed under reduced pressure to give (R)-[1-(4-bromo-phenyl)-ethyl]-carbamic acid tert-butyl ester (1.8 g, 6.0 mmol, 120%) as a white solid. To a solution of (R)-[1-(4-bromo-phenyl)-ethyl]-carbamic acid tert-butyl ester (0.73 g, 2.4 mmol) in 1,2-dimethoxyethane (10 ml) was added tetrakis (triphenylphosphine) palladium (0.14 g, 0.12 mmol), 2-chloropyridine-3-boronic acid (0.77 g, 4.9 mmol) and 2 M sodium carbonate. The reaction mixture was heated to reflux for 16 h and the solvent removed under reduced pressure. The residue was partitioned between ethyl acetate and water. The organic phase was washed with brine, dried over anhydrous magnesium sulfate and the solvent removed under reduced pressure. The residue was chromatographed over silica gel eluting with 3:1 heptane/ethyl acetate and the solvent removed under reduced pressure to give (R)-{1-[4-(2-chloro-pyridin-3-yl)-phenyl]-ethyl}-carbamic acid tert-butyl ester (0.56 g, 1.7 mmol, 71%) as an off white solid. A mixture of (R)-{1-[4-(2-chloro-pyridin-3-yl)-phenyl]-ethyl}carbamic acid tert-butyl ester (100 mg, 0.3 mmol), sodium ethoxide (61 mg, 0.9 mmol) and tetrahydrofuran (5 ml) was heated under reflux under an argon atmosphere for 16 h. The solvent was evaporated and the residue purified on a SCX column (eluted with 2M ammonia in methanol) chromatography to give (R)-1-[4-(2-ethoxy-pyridin-3-yl)-phenyl]-ethylamine (66 mg, 0.27 mmol, 90%) as a yellow gum. To a solution of (R)-1-[4-(2-ethoxy-pyridin-3-yl)-phenyl]-ethylamine (13 mg, 0.05 mmol) in dichloromethane (1 ml) was added triethylamine (17 mg, 0.16 mmol) followed by 2-(trifluoromethoxy)benzenesulfonyl chloride (17 mg, 0.065 mmol). The reaction mixture was stirred for 16 h and the solvent evaporated under reduced pressure. The crude product was taken up in dimethyl sulfoxide (1 ml) and purified by preparatory LCMS. The solvent was evaporated under reduced pressure to give the title compound (6 mg, 0.013 mmol, 26%). $^1$H NMR (400 MHz, DMSO-d$_6$): δ 8.42 (d, 1H), 8.13 (dd, 1H), 7.81 (dd, 1H), 7.63 (m, 2H), 7.39 (m, 4H), 7.24 (d, 2H), 7.05 (m, 1H), 4.48 (q, 1H), 4.36 (q, 2H), 1.35 (d, 3H), 1.29 (t, 3H) ppm; MS (ESI) m/z: 467 [M+H]$^+$.

EXAMPLE 9

N-(2-Ethoxy-2'-methoxy-5'-methyl-biphenyl-4-ylmethyl)-2-trifluoromethoxy-benzenesulfonamide Prepared in a similar manner to N-(5'-fluoro-2,2'-dimethoxy-biphenyl-4-ylmethyl)-4-methoxy-benzenesulfonamide (Example 6) starting with trifluoro-methanesulfonic acid-4-formyl-2-ethoxy-phenyl ester and 2-methyl-5-methoxyphenyl boronic acid. Title compound: MS (ESI) m/z: 500.0 [M+H]$^+$.

EXAMPLE 10

(R)-2,5-Dimethyl-furan-3-sulfonic acid [1-(5'-fluoro-2'-methoxy-biphenyl-4-yl)-ethyl]-amide Triethylamine (41.1 µl, 0.295 mmol) then 2,5-dimethyl-3-furansulfonyl chloride (19.1 mg, 0.0982 mmol) were added to a solution of 1-(5'-fluoro-2'-methoxy-biphenyl-4-yl)-ethylamine (20 mg, 0.082 mmol) in dichloromethane (1 ml) and the resulting solution shaken at room temperature overnight. The reaction mixture was washed with saturated sodium bicarbonate solution (500 µl) and the organic phase separated, dried over anhydrous magnesium sulfate and the solvent evaporated. The crude product was purified by preparatory LCMS. The solvent was evaporated under reduced pressure to give the title compound (3.9 mg, 0.0097 mmol, 11.8%). $^1$H NMR (400 MHz, CDCl$_3$): δ 7.40, 7.23 (a/b, 4H), 7.05-6.88 (m, 3H), 5.99 (s, 1H), 4.67 (m, 1H), 4.55 (m, 1H), 3.78 (s, 3H), 2.35 (s, 3H), 2.17 (s, 3H), 1.52 (d, 3H) ppm; MS (ESI) m/z: 426 [M+Na]$^+$.

EXAMPLE 11

(R)-1-Methyl-3-trifluoromethyl-1H-pyrazole-4-sulfonic acid [1-(5'-fluoro-2'-methoxy-biphenyl-4-yl)-ethyl]-amide Prepared in a similar manner to (R)-2,5-dimethyl-furan-3-sulfonic acid [1-(5'-fluoro-2'-methoxy-biphenyl-4-yl)-ethyl]-amide (Example 10) starting with 1-methyl-3-(trifluoromethyl)-1H-pyrazole-4-sulfonyl chloride and 1-(5'-fluoro-2'-methoxy-biphenyl-4-yl)-ethylamine. Title compound: $^1$H NMR (400 MHz, CDCl$_3$): δ 7.40, 7.16 (a/b, 4H), 7.05-6.88 (m, 3H), 4.89 (m, 1H), 4.60 (t, 1H), 3.80 (s, 3H), 3.72 (s, 3H), 1.52 (d, 3H) ppm; MS (ESI) m/z: 480 [M+Na]$^+$.

EXAMPLE 12

(R)-2,5-Dichloro-thiophene-3-sulfonic acid [1-(5'-fluoro-2'-methoxy-biphenyl-4-yl)-ethyl]-amide Prepared in a similar manner to (R)-2,5-dimethyl-furan-3-sulfonic acid [1-(5'-fluoro-2'-methoxy-biphenyl-4-yl)-ethyl]-amide (Example 10) starting with 2,5-dichloro-3-thiophenesulfonyl chloride and 1-(5'-fluoro-2'-methoxy-biphenyl-4-yl)-ethylamine. Title compound: $^1$H NMR (400 MHz, CDCl$_3$): δ 7.40, 7.18 (a/b, 4H), 7.05-6.88 (m, 4H), 5.05 (d, 1H), 4.60 (m, 1H), 3.78 (s, 3H), 1.54 (d, 3H) ppm; MS (ESI) m/z: 482 [M+Na]$^+$.

EXAMPLE 13

(R)-1,3-Dimethyl-1H-pyrazole-4-sulfonic acid [1-(5'-fluoro-2'-methoxy-biphenyl-4-yl)-ethyl]-amide Prepared in a similar manner to (R)-2,5-dimethyl-furan-3-sulfonic acid [1-(5'-fluoro-2'-methoxy-biphenyl-4-yl)-ethyl]-amide (Example 10) starting with 1,3-dimethyl-1H-pyrazole-4-sulfonyl chloride and 1-(5'-fluoro-2'-methoxy-biphenyl-4-yl)-ethylamine. Title compound: $^1$H NMR (400 MHz, CDCl$_3$): δ 7.41, 7.20 (a/b, 4H), 7.39 (s, 1H), 7.05-6.88 (m, 3H), 4.70 (d, 1H), 4.55 (m, 1H), 3.78 (s, 3H), 3.69 (s, 3H), 2.33 (s, 3H), 1.52 (d, 3H) ppm; MS (ESI) m/z: 404 [M+H]$^+$.

EXAMPLE 14

(R)-4-Bromo-thiophene-3-sulfonic acid {1-[4-(2-methoxy-pyridin-3-yl)-phenyl]-ethyl}-amide 2M Aqueous sodium carbonate solution (3.25 ml, 6.50 mmol) was added to a mixture of 2-methoxypyridine-3-boronic acid (994 mg, 6.50 mmol), (R)-[1-(4-bromo-phenyl)-ethyl]-carbamic acid tert-butyl ester (650 mg, 2.16 mmol) and tetrakis(triphenylphosphine)palladium (0) (125 mg, 0.108 mmol) in 1,2 dimethoxyethane (27 ml). The mixture was heated at 95° C. for 16 h under nitrogen atmosphere. The solvent was evaporated and the residue partitioned between ethyl acetate and water. The organic phase was washed twice with brine, dried over anhydrous magnesium sulfate and the solvent evaporated. The resulting gum was chromatographed over silica gel eluting with heptane/dichloromethane and the solvent evaporated to give (R)-{1-[4-(2-methoxy-pyridin-3- yl)-phenyl]-ethyl}-carbamic acid tert-butyl ester (593 mg, 1.71 mmol, 83.5%) as a crystalline solid. Trifluoroacetic acid (6.45 ml, 86.8 mmol) was added dropwise to a solution of (R)-{1-[4-(2-methoxy-pyridin-3-yl)-phenyl]-ethyl}carbamic acid tert-butyl ester (645 mg, 1.97 mmol) in dichloromethane (6.45 ml) under a nitrogen atmosphere at 0° C. After stirring for 1 h at 0° C. the solvent was evaporated. Methanol (20 ml) was added and the mixture added to a Strata™ 5 g/20 ml SCX column. The intermediate amine was eluted with 2M ammonia in methanol. The solvent was evaporated to give (R)-1-[4-(2-methoxy-pyridin-3-yl)-phenyl]-ethylamine as a gum (425 mg, 1.86 mmol, 94.6%). The title compound was then prepared in a similar manner to (R)-2,5-dimethyl-furan-3-sulfonic acid [1-(5'-fluoro-2'-methoxy-biphenyl-4-yl)-ethyl]-amide (Example 10) using 4-bromo-3-thiophenesulfonyl chloride and 1-[4-(2-Methoxy-pyridin-3-yl)-phenyl]-ethylamine. Title compound: $^1$H NMR (400 MHz, CDCl$_3$): δ 8.17 (d, 1H), 7.56 (d, 1H), 7.41, 7.20 (a/b, 4H), 7.38 (m, 1H), 6.99-6.92 (m, 2H), 5.27 (d, 1H), 4.60 (m, 1H), 3.97 (s, 3H), 1.54 (d, 3H) ppm; MS (ESI) m/z: 453 [M+H]$^+$.

EXAMPLE 15

N-[2,2,2-Trifluoro-1-(5'-fluoro-2'-methoxy-biphenyl-4-yl)-ethyl]-2-trifluoromethoxy-benzenesulfonamide To a solution of 4-bromobenzaldehyde (3.06 g, 16.5 mmol) in toluene (60 ml) was added 5-fluoro-2-methoxyphenyl boronic acid (3.10 g, 18.2 mmol), 2M sodium carbonate solution (16.5 ml) and tetrakis(triphenylphosphine)palladium (0) (1 g, 0.86 mmol). The solution was refluxed for 48 h then cooled to ambient temperature, washed with water, brine and dried over anhydrous sodium sulfate. Evaporation of solvent gave a residue that was flash chromatographed over silica gel eluting with 1:1 ethyl acetate/heptane. Evaporation of solvent gave 5'-fluoro-2'-methoxy-biphenyl-4-carbaldehyde (2.63 g) as a crystalline solid. To a solution of 5'-fluoro-2'-methoxy-biphenyl-4-carbaldehyde (1.5 g, 6.9 mmol) in tetrahydrofuran (20 ml) was added titanium tetraisopropoxide (10 ml) and (±)-tert-butyl sulfinamine. The solution was stirred for 48 h then poured into brine and dichloromethane added with stirring. The organic layer was separated, dried over anhydrous magnesium sulfate and the solvent evaporated. Heptane was added to the oil which induced crystallisation and gave 2-methyl-propane sulfinic acid 5'-fluoro-2'-methoxy-biphenyl-4-ylmethylene amide (1.85 g) as a white solid. To a solution of 2-methyl-propane sulfinic acid 5'-fluoro-2'-methoxy-biphenyl-4-ylmethylene amide (1 g, 3 mmol) and tetrabutyl ammonium difluorotriphenylsilicagelte (1.8 g, 3.3 mmol) in tetrahydrofuran (50 ml) at −55° C. was added trifluoromethyltrimethylsilane with stirring. The reaction mixture was kept below −40° C. for 3 h then warmed to −10° C. for 1 h. The reaction mixture was cooled to −30° C. then quenched with saturated ammonium chloride solution and extracted with ethyl acetate. The organic phase was dried over anhydrous magnesium sulfate, evaporated to a low volume and heptane added. The crystalline 2-methyl-propane sulfinic acid [2,2,2-trifluoro-1-(5'-fluoro-2'-methoxy-biphenyl-4-yl)-ethyl]-amide (0.75 g) was collected by filtration. To a solution of 2-methyl-propane sulfinic acid [2,2,2-trifluoro-1-(5'-fluoro-2'-methoxy-biphenyl-4-yl)-ethyl]-amide (0.73 g, 1.8 mmol) in methanol (10 ml) at room temperature was added a 1M solution of Hydrogen chloride in ether with stirring. The reaction mixture was stirred for 2 h, then the solvent was evaporated and ether added. The crystalline 2,2,2-trifluoro-1-(5'-fluoro-2'-methoxy-biphenyl-4-yl)-ethylamine hydrochloride (0.38 g) was collected by filtration. To a solution of 2,2,2-trifluoro-1-(5'-fluoro-2'-methoxy-biphenyl-4-yl)-ethylamine hyrochloride (60 mg, 0.15 mmol) in pyridine (3 ml) was added 2-trifluoromethoxyphenyl sulfonyl chloride with stirring. The reaction was stirred for 3 days at 100° C. then cooled to room temperature and 5M Hydrogen chloride and dichloromethane added. The organic layer was separated and the solvent evaporated. The residue was flash chromatographed over silica gel eluting with 1:1 heptane/dichloromethane and the solvent evaporated to give the title compound (29 mg). $^1$H NMR (400 MHz, CDCl$_3$): 7.58-7.41 (m, 4H), 7.27-7.11 (m, 3H), 7.04-6.90 (m, 3H), 5.51 (d, 1H), 5.00 (app quin, 1H), 3.78 (s, 3H) ppm; MS (ESI) m/z: 546 [M+Na]$^+$.

EXAMPLE 16

N-(5'-Fluoro-3,2'-dimethoxy-biphenyl-4-ylmethyl)-4-trifluoromethoxy-benzenesulfonamide A mixture of 2-methoxy-4-hydroxybenzaldehyde (0.304 g, 2.0 mmol), N-phenyl-bis(trifluoromethane) sulfonamide (0.714 g, 2.0 mmol) and potassium carbonate (0.814 g, 6 mmol) in tetrahydrofuran (3.0 ml) was heated in a microwave oven at 120° C. for 6 min. 5-Fluoro-2-methoxyphenyl boronic acid (0.680 g, 4 mmol), tetrakis(triphenylphosphine) palladium (0) (0.05 g, 0.04 mmol) and dimethylformamide (1 ml) were then added and the mixture heated in a microwave oven at 120° C. for 10 min. Ethyl acetate was added and the solution washed with saturated aqueous sodium bicarbonate solution and dried over anhydrous sodium sulfate. The solvent was evaporated and the residue flash chromatographed on silica gel eluting with 7:3 heptane/ethyl actate. Evaporation of the solvent gave 5'-fluoro-3-2'-dimethoxy-biphenyl-4-carbaldehyde (0.457 g) as a solid. The title compound was prepared in a similar manner to N-(5'-fluoro-2,2'-dimethoxy-biphenyl-4-ylmethyl)-4-methoxy-benzenesulfonamide (Example 6) using 5'-fluoro-3-2'-dimethoxy-biphenyl-4-carbaldehyde instead of 5'-fluoro-2,2'-dimethoxy-biphenyl-4-carbaldehyde to give C-(5'-fluoro-3,2'-dimethoxy-biphenyl-4-yl)-methylamine and 4-trifluoromethoxybenzene sulfonyl chloride instead of 4-methoxybenzene sulfonyl chloride. Title compound: MS (ESI) m/z: 486.4 [M+H]$^+$.

EXAMPLE 17

N-(5'-Fluoro-3,2'-dimethoxy-biphenyl-4-ylmethyl)-4-fluoro-benzenesulfonamide

Prepared in a similar manner to N-(5'-Fluoro-3,2'-dimethoxy-biphenyl-4ylmethyl)-4-trifluoromethoxy-benzenesulfonamide (Example 16) starting with 4-fluorobenzene sulfonyl chloride and C-(5'-fluoro-3,2'-dimethoxy-biphenyl-4-yl)-methylamine. Title compound: $^1$H NMR (400 MHz, CDCl$_3$): 7.7-7.8 (m, 2H), 7.0-7.1 (m, 2H), 6.85-7.15 (m, 6H), 5.06-5.15 (m, 1H), 4.21 (d, 2H), 3.76 (s, 3H), 3.77 (s, 3H) ppm; MS (ESI) m/z: 442.0 [M+Na]$^+$.

EXAMPLE 18

3,4-Difluoro-N-(2'-methoxy-biphenyl-4-ylmethyl)-benzenesulfonamide

2'-Methoxy-biphenyl-4-carbaldehyde-O-methyl-oxime was prepared in a similar manner to 5'-fluoro-2,2'-dimethoxy-biphenyl-4-carbaldehyde-O-methyl-oxime (Example 6) using 2'-methoxy-biphenyl-4-carbaldehyde. C-(2'-

Methoxy-biphenyl-4-yl)-methylamine was then prepared in a similar manner to C-(5'-fluoro-2,2'-dimethoxy-biphenyl-4-yl)-methylamine (Example 6) using 2'-methoxy-biphenyl-4-carbaldehyde-O-methyl-oxime. The title compound was prepared in a similar manner to N-(5'-fluoro-2,2'-dimethoxy-biphenyl-4-ylmethyl)-4-methoxy-benzenesulfonamide (Example 6) using C-(2'-methoxy-biphenyl-4-yl)-methylamine and 3,4-difluorobenzene sulfonyl chloride. MS (ESI) m/z: 388.1 [M+H]$^+$.

EXAMPLE 19

(R)—N-{1-[3-Methoxy-4-(2-methoxy-pyridin-3yl)-phenyl]-ethyl}-2-trifluoromethoxy-benzenesulfonamide A mixture of acetovanillone (0.332 g, 2.0 mmol), N-phenyl-bis(trifluoromethane-sulfonimide) (710 mg, 2.0 mmol), potassium carbonate (830 mg, 6.0 mmol) and tetrahydrofuran (3.0 ml) was heated to 120° C. for 6 min in a microwave oven. 2-Methoxypyridine-3-boronic acid (611 mg, 4 mmol), tetrakis(triphenylphosphine)palladium (0) (115 mg, 100 μmol), N-methylpyrrolidinone (1 ml) were then added and the mixture heated in the microwave at 120° C. for 10 min. The reaction mixture was partitioned between ethyl acetate and saturated aqueous sodium bicarbonate solution. The organic phase was separated and washed with saturated aqueous sodium bicarbonate solution, dried over anhydrous magnesium sulfate and the solvent evaporated to give 1-[3-methoxy-4-(2-methoxy-pyridin-3yl)-phenyl]-ethanone in quantitative yield. Reductive amination with ammonium acetate (20 equivalents) in methanol (50 ml) containing sodium cyanoborohydride (1 equivalent) followed by aqueous workup with saturated aqueous sodium bicarbonate and extraction into ethyl actetate gave, after solvent was evaporated 1-[3-methoxy-4-(2-methoxy-pyridin-3yl)-phenyl]-ethylamine.
To 1-[3-methoxy-4-(2-methoxy-pyridin-3yl)-phenyl]-ethylamine was added 2-trifluoromethoxy-benzenesulfonyl chloride (1 equivalent) in dichloromethane, diisopropylethylamine (4 equivalents) and the mixture overnight. The racemic product was isolated by normal phase HPLC on silica gel eluting with heptane/ethyl acetate and the solvent evaporated to give a clear oily solid (72 mg). $^1$H NMR (400 MHz, CDCl$_3$): δ 8.15 (d, 1H), 7.9 (d, 1H), 7.5 (m, 1H), 7.4 (m, 1H), 7.3-7.2 (m, 2H), 7.05 (d, 1H), 6.9 (m, 1H), 6.75-6.65 (m, 2H), 5.0 (d, 1H), 4.55 (m, 1H), 3.91 (s, 3H), 3.67 (s, 3H), 1.51 (d, 3H) ppm; MS (ESI) m/z: 483.3 [M+1]$^+$. The racemate was resolved by chiral HPLC (CHIRALPAK-AS, eluting with 9:1 isohexane/ethanol) to give the title compound (11 mg) and its enantiomer (11) mg.

EXAMPLE 20

1-Methyl-3-trifluoromethyl-1H-pyrazole-4-sulfonic-acid (5'-fluoro-2,2'-dimethoxy-biphenyl-4-ylmethyl)-amide Prepared in a similar manner to N-(5'-fluoro-2,2'-dimethoxy-biphenyl-4ylmethyl)-4-methoxy-benzenesulfonamide (Example 6) using 1-methyl-3-(trifluoromethyl)-1H-pyrazole-4-sulfonyl chloride instead of 4-methoxybenzene sulfonyl chloride. Title compound: MS (ESI) m/z: 474.0 [M+H]$^+$.

EXAMPLE 21

4-Bromo-thiophene-3-sulfonic acid (5'-fluoro-2,2'-dimethoxy-biphenyl-4-ylmethyl)-amide Prepared in a similar manner to N-(5'-fluoro-2,2'-dimethoxy-biphenyl-4ylmethyl)-4-methoxy-benzenesulfonamide (Example 6) using 1-bromothiophene-4-sulfonyl chloride instead of 4-methoxybenzene sulfonyl chloride. Title compound: MS (ESI) m/z: 488.1 [M+H]$^+$.

EXAMPLE 22

N-(2-Benzyloxy-5'-fluoro-2'-methoxy-biphenyl-4-ylmethyl)-2-trifluoromethoxy-benzenesulfonamide To a stirred solution of 3-hydroxy-4-iodobenzaldehyde (4.0 g, 16.2 mmol) in acetone (50 ml) was added benzyl bromide (2.76 g, 16.2 mmol) and potassium carbonate (2.23 g, 16.2 mmol). The reaction mixture was heated under reflux for 16 h. The solvent was evaporated and the residue was dissolved in ethyl acetate, washed with water and dried over anhydrous magnesium sulfate. The solvent was evaporated to give 3-benzyloxy-4-iodo-benzaldehyde (5.1 g) as orange oil. A mixture of 3-benzyloxy-4-iodobenzaldehyde (1.05 g, 3.24 mmol), 5-fluoro-2-methoxyphenyl boronic acid (1.12 g 6.6 mmol), potassium carbonate (1.22 g, 8.8 mmol) and tetrakis (triphenylphosphine)palladium (0) (0.40 g, 0.35 mmol) in tetrahydrofuran (12.0 ml) and dimethylformamide (4 ml) was heated in a microwave oven at 120° C. for 30 min. The reaction mixture was diluted with diethyl ether, washed with 2M sodium hydroxide and dried over anhydrous magnesium sulfate. The solvent was evaporated and the residue flash chromatographed over silica gel eluting with 5:1 heptane/ethyl acetate to give 2-benzyloxy-5'-fluoro-2'-methoxy-biphenyl-4-carbaldehyde. To a stirred solution of 2-benzyloxy-5'-fluoro-2'-methoxy-biphenyl-4-carbaldehyde (0.50 g, 1.5 mmol) was added 2-methyl-2-propane sulfinamide (0.183 g, 1.51 mmol) and titanium(IV) isopropoxide (3 ml, 7.5 mmol) in tetrahydrofuran (10 ml). The reaction mixture was stirred at ambient temperature under nitrogen atmosphere for 16 h. Brine was added to reaction mixture which was then filtered through dicalite and extracted with dichloromethane The extract was dried over anhydrous sodium sulfate, the solvent evaporated and the residue flash chromatographed over silica gel eluting with 8:2 heptane/ethyl acetate to give 2-methyl-propane-2-sulfininic acid-2-benzyloxy-5'-fluoro-2'-methoxy-biphenyl-4-ylmethylene amide (0.3 g). To a stirred solution of 2-methyl-propane-2-sulfininic acid-2-benzyloxy-5'-fluoro-2'-methoxy-biphenyl-4-ylmethylene amide (0.3 g, 0.7 mmol) in dichloromethane (20 ml) was added diisobutylaluminium hydride (1M in tetrahydrofuran, 6 ml, 4.2 mmol) at −78° C. under nitrogen atmosphere. The reaction mixture warmed to ambient temperature over 16 h. Potassium sodium L-tartrate tetrahydrate was added and the mixture stirred for 30 min then extracted with ethyl acetate. The extract was washed with water, dried over anhydrous sodium sulfate and the solvent evaporated to give 2-methyl-propane-2-sulfininic acid-(2-benzyloxy-5'-fluoro-2'-methoxy-biphenyl-4-ylmethylene) amide (0.250 g). To a stirred solution of 2-methyl-propane-2-sulfininic acid-(2-benzyloxy-5'-fluoro-2'-methoxy-biphenyl-4-ylmethylene) amide (0.25 g, 0.57 mmol) in methanol (5 ml) was added Hydrogen chloride (1M in diethyl ether). The solution was left to stir at ambient temperature for 10 min and the solvent evaporated. The residue was dissolved in dichloromethane and purified on a SCX column (eluted with 2M ammonia in methanol) to give C-(2-Benzyloxy-5'-methoxy-biphenyl-4-yl)-methylamine (0.12 g). The title compound was then prepared in a similar manner to N-(5'-fluoro-2,2'-dimethoxy-biphenyl-4-ylmethyl)-4-methoxy-benzenesulfonamide (Example 6) using C-(2-benzyloxy-5'- methoxy-biphenyl-4-yl)-methylamine and 2-trifluromethoxybenzene sulfonyl chloride. MS (ESI) m/z: 562.2 [M+H]+.

EXAMPLE 23

(R)-4-Bromo-2-trifluoromethoxy-N-[1-(2'-trifluoromethoxy-biphenyl-4yl)-ethyl]-benzenesulfonamide Prepared in a similar manner to (R)-5-methyl-2-trifluoromethyl-furan-3-sulfonic acid [1-(2'-trifluoromethoxy-biphenyl-4-yl)-ethyl]-amide (Example 3) using 4-bromo-2-trifluoromethoxybenzene sulfonyl chloride instead of 5-methyl-2-trifluoromethyl-4-furan-3-sulfonyl chloride. Title compound: $^1$H NMR (400 MHz, DMSO-$d_6$): δ 8.65 (d, 1H), 7.7 (d, 1H), 7.6 (d, 1H), 7.55-7.4 (m, 5H), 7.25 (s, 4H), 4.5 (m, 1H), 1.38 (d, 3H) ppm; MS (ESI) m/z: 584.0 [M–H]−.

EXAMPLE 24

3,5-Dimethyl-isoxazole-4-sulfonic acid [1-(5'-fluoro-2'-methoxy-2,6-dimethyl-biphenyl-4-yl)-ethyl]-amide 1-(5'-Fluoro-2'-methoxy-2,6-dimethyl-biphenyl-4-yl)-ethylamine was prepared in a similar manner to 1-(2-allyl-5'-fluoro-2'-methoxy-biphenyl-4-yl)-ethylamine (Example 34) using 3,5-dimethyl-4-hydroxy acetophenone instead of 3'-allyl-4'-hydroxyacetophenone. The title compound was prepared in a similar manner to N-[1-(2-allyl-5'-fluoro-2'-methoxy-biphenyl-4-yl)-ethyl]-3,4-difluoro-benzenesulfonamide (Example 34) using 1-(5'-fluoro-2'-methoxy-2,6-dimethyl-biphenyl-4-yl)-ethylamine and 3,5-dimethyl-isoxazole-4-sulfonyl chloride. MS (ESI) m/z: 433.3 [M+H]+.

EXAMPLE 25

(R)-3,4-Difluorobenzenesulfonic acid [1-(5'-chloro-2'-methoxy-biphenyl-4-yl)-ethyl]-amide (R)-1-(5'-Chloro-2'-methoxy-biphenyl-4-yl)-ethylamine was prepared in a similar manner to (R)-1-[4-(5-chloro-2-methoxypyridin-3-yl)-phenyl]ethylamine (Example 39) starting from (R)-[1-(4-bromophenyl)-ethyl]-carbamic acid and 5-chloro-2-methoxyphenylboronic acid. The title compound was prepared in a similar manner to (R)-1-Methyl-3-trifluoromethyl-1H-pyrazole-4-sulfonic acid 1-{[4-(5-chloro-2-methoxypyridin-3-yl)-phenyl]-ethyl}-amide (Example 39) using (R)-1-(5'-chloro-2'-methoxy-biphenyl-4-yl)-ethylamine and 3,4-difluorobenzenesulfonyl chloride. $^1$H NMR (400 MHz, CDCl$_3$): 7.52-7.42 (m, 2H), 7.35-7.08 (m, 7H), 6.90 (m, 1H), 4.80 (d, 1H), 4.60 (q, 1H), 3.79 (s, 3H), 1.51 (d, 3H) ppm.

EXAMPLE 26

(R)-1-Methyl-3-trifluoromethyl-1H-pyrazole-4-sulfonic acid {1-[4-(2-difluoromethoxy-pyridin-3-yl)-phenyl]-ethyl}-amide A mixture of (R)-1-(4-bromophenyl)ethylamine (3.12 g, 15.6 mmol), pthalic anhydride (2.31 g, 15.6 mmol) and dimethylformamide (20 ml) was heated in a microwave oven at 210° C. for 20 min. The reaction mixture was then partitioned between diethyl ether and water, and the organic phase washed with brine. The solvent was evaporated to give (R)-2-[1-(4-bromo-phenyl)-ethyl]-isoindole-1,3-dione (3.44 g, 10.4 mmol, 67%). A mixture of 2-methoxypyridine-3-boronic acid (4.0 g, 26 mmol), (R)-2-[1-(4-bromo-phenyl)-ethyl]-isoindole-1,3-dione (2.88 g, 8.7 mmol), tetrakis(triphenylphosphine)palladium (0) (0.5 g, 0.44 mmol), 1,2-dimethoxyethane (50 ml) and 2 M aqueous sodium carbonate (14.4 ml, 28.8 mmol) were heated in a microwave oven at 150° C. for 15 min. The reaction mixture was partitioned between ethyl acetate and water. The organic phase was washed with water, brine and the solvent evaporated. The residue was chromatographed on silica gel eluting with 6:1 heptane/ethyl acetate to give (R)-2-{1-[4-(2-methoxy-pyridin-3-yl)-phenyl]-ethyl}-isoindole-1,3-dione (1.38 g, 3.9 mmol, 45%). A mixture of (R)-2-{1-[4-(2-methoxy-pyridin-3-yl)-phenyl]-ethyl}-isoindole-1,3-dione (1.38 g, 3.9 mmol) and pyridine.hydrogen chloride (4.45 g, 3.9 mmol) was heated in a microwave oven at 210° C. for 10 min. The reaction mixture was then partitioned between ethyl acetate and water. The organic phase was dried over anhydrous magnesium sulfate and the solvent evaporated to give (R)-2-{1-[4-(2-hydroxy-pyridin-3-yl)-phenyl]-ethyl}-isoindole-1,3-dione (1.38 g, 4.0 mmol, 103%). To a solution of (R)-2-{1-[4-(2-hydroxy-pyridin-3-yl)-phenyl]-ethyl}-isoindole-1,3-dione (1.20 g, 3.5 mmol) in dimethylformamide (30 ml) was added caesium carbonate (1.93 g, 7.7 mmol) and chlorodifluoromethyl acetate (1.11 g, 7.7 mmol). The reaction mixture was heated to 120° C. for 4 h under nitrogen atmosphere. The reaction was partitioned between diethyl ether and water. The organic phase was washed with brine and the solvent evaporated. The residue was chromatographed on silica gel eluting with 3:1 heptane/ethyl acetate to give (R)-2-{1-[4-(2-difluoromethoxy-pyridin-3-yl)-phenyl]-ethyl}-isoindole-1,3-dione (136 mg, 0.34 mmol, 10%). A mixture of (R)-2-{1-[4-(2-difluoromethoxy-pyridin-3-yl)-phenyl]-ethyl}-isoindole-1, 3-dione (220 mg, 0.34 mmol), hydrazine hydrate (136 mg, 0.34 mmol) and methanol (5.3 ml) was stirred at room temperature for 16 h under nitrogen atmosphere. The solvent was evaporated and dichloromethane (5 ml) added. The solid was filtered off and the solvent was evaporated from the filtrates. The residue was purified on a SCX column (eluted with 2M ammonia in methanol) to give (R)-1-[4-(2-difluoromethoxy-pyridin-3-yl)-phenyl]-ethylamine (72 mg, 0.27 mmol, 79%). To a solution of (R)-1-[4-(2-difluoromethoxy-pyridin-3-yl)-phenyl]-ethylamine (35 mg, 0.13 mmol) in dichloromethane (1 ml) was added triethylamine (41 mg, 0.40 mmol) and the 1-methyl-3-(trifluoromethyl)-1H-pyrazole-4-sulfonylchloride (39 mg, 0.16 mmol). The reaction mixture was agitated for 16 hours then the solvent evaporated and the residue chromatographed on silica gel (eluting with 1:1 heptane/ethyl acetate) to give the title compound (29 mg, 0.06 mmol, 46%). $^1$H NMR (400 MHz, CDCl$_3$): δ 8.18 (dd, 1H), 7.71 (d, 1H), 7.60 (t, 1H), 7.47 (s, 1H), 7.42 (d, 2H), 7.19-7.25 (m, 3H), 5.11 (bd, 1H), 4.62 (m, 1H), 3.74 (s, 3H), 1.51 (d, 3H) ppm; MS (ESI) m/z: 477.1 [M+H]+.

EXAMPLE 27

(R)-1-Difluoromethyl-3-methyl-1H-pyrazole-4-sulfonic acid [1-(2'-trifluoromethoxy-biphenyl-4-yl)-ethyl]-amide Palladium acetate (34 mg, 0.150 mmol) was added to a mixture of 2-(trifluoromethoxy)phenylboronic acid (773 mg, 3.75 mmol) and (R)-(+)-1-(4-bromophenyl)ethylamine (300 mg, 1.50 mmol) in water (12 ml). This mixture was heated in a microwave oven at 150° C. for 10 min, then diluted with methanol (200 ml) and purified on a SCX column (eluted with 2M ammonia in methanol) to give (R)-1-(2'-trifluoromethoxy-biphenyl-4-yl)-ethylamine (345 mg, 1.23 mmol, 81.9%) as a gum. The title compound was then prepared in a similar manner to (R)-2,5-dimethyl-furan-3-sulfonic acid [1-(5'-fluoro-2'-methoxy-biphenyl-4-yl)-ethyl]-amide (Example 10) using 1-difluoromethyl-3-methylpyrazole-4-sulfonyl chloride and (R)-1-(2'-trifluoromethoxy-biphenyl-4-yl)-ethylamine. Title compound: $^1$H NMR (400 MHz, CDCl$_3$): δ 7.95 (s, 1H), 7.42-7.16 (m, 8H), 6.97 (s, 1H), 4.88 (d, 1H), 4.52 (m, 1H), 2.30 (s, 3H), 1.56 (d, 3H) ppm; MS (ESI) m/z: 476 [M+H]$^+$.

EXAMPLE 28

(R)-1-Difluoromethyl-3,5-dimethyl-1H-pyrazole-4-sulfonic acid [1-(2'-trifluoromethoxy-biphenyl-4-yl)-ethyl]-amide Prepared in a similar manner to (R)-2,5-dimethyl-furan-3-sulfonic acid [1-(5'-fluoro-2'-methoxy-biphenyl-4-yl)-ethyl]-amide (Example 10) starting with 1-difluoromethyl-3,5-dimethylpyrazole-4-sulfonyl chloride and 1-(2'-trifluoromethoxy-biphenyl-4-yl)-ethylamine. Title compound: $^1$H NMR (400 MHz, CDCl$_3$): δ 7.43-7.11 (m, 8H), 6.99 (s, 1H), 4.86 (s, 1H), 4.58 (m, 1H), 2.45 (s, 3H), 2.30 (s, 3H), 1.54 (d, 3H), ppm; MS (ESI) m/z: 490 [M+H]$^+$.

EXAMPLE 29

2-Chloro-N-[1-(3-chloro-5'-fluoro-2'-methoxy-biphenyl-4-yl)-ethyl]-4-cyano-benzenesulfonamide To a stirred solution of 4-bromo-2-chloro-acetophenone (4.66 g, 20 mmol) in methanol (50 ml) under nitrogen atmosphere was added ammonium acetate (29 g, 0.4 mol) and sodium cyanoborohydride (1.21 g, 20 mmol). The reaction mixture was stirred at ambient temperature for 10 days. The solvent was evaporated and the residue partitioned between dichloromethane and aqueous sodium carbonate solution. The organic phase was dried over anhydrous sodium sulfate and the solvent evaporated. The residue was dissolved in diethyl ether and treated with 2M Hydrogen chloride in diethyl ether The resulting precipitate was filtered and dried to give 1-(4-bromo-2-chloro-phenyl)-ethylamine hydrochloride (3.2 g). A mixture of 1-(4-bromo-2-chloro-phenyl)-ethylamine hydrochloride (0.25 g, 1.07 mmol), 5-fluoro-2-methoxyphenyl boronic acid (0.364 g, 2.14 mmol), palladium acetate (0.005 g, 0.021 mmol) in water (4 ml) was heated in a microwave oven at 190° C. for 4 min. The mixture was added to a SCX column (eluted with 1:1 dichloromethane/methanol then 10% 7M ammonia/methanol) and solvent evaporated to give 1-(3-chloro-5'-fluro-2'-methoxy-biphenyl-4-yl)-ethylamine (0.266 g). The title compound was prepared in a similar manner to N-(5'-fluoro-2,2'-dimethoxy-biphenyl-4-ylmethyl)-4-methoxy-benzenesulfonamide (Example 6) using 1-(3-chloro-5'-fluoro-2'-methoxy-biphenyl-4-yl)-ethylamine and 2-chloro-4-cyanobenzene sulfonyl chloride instead of 4-methoxybenzene sulfonyl chloride: $^1$H NMR (400 MHz, DMSO-d$_6$): δ 9.1 (d 1H), 8.1 (s, 1H), 7.9 (d, 1H), 7.8 (d, 1H), 7.5 (d, 1H), 7.3 (d, 2H), 7.2 (m, 1H), 7-7.18 (m, 2H), 4.9 (m, 1H), 3.8 (s, 3H), 1.4 (d, 3H) ppm. MS (ESI) m/z: value [M+H]$^+$.

EXAMPLE 30

1-Methyl-3-trifluoromethyl-1H-pyrazole-4-sulfonic acid [1-(3,5'-difluoro-2'-methoxy-biphenyl-4-yl)-ethyl]-amide 1-(3,5'-Difluoro-2'-methoxy-biphenyl-4-yl)-ethylamine was prepared in a similar manner to 1-(2-allyl-5'-fluoro-2'-methoxy-biphenyl-4-yl)-ethylamine (Example 34) using 4'-bromo-2'-fluoroacetophenone to give 1-(4-bromo-2-fluoro-phenyl)-ethylamine. To a solution of 1-(3,5'-difluoro-2'-methoxy-biphenyl-4-yl)-ethylamine (20.0 mg, 0.08 mmol) in dichloromethane (1 ml) was added triethylamine (8.1 mg, 0.08 mmol) and 1-methyl-3-trifluoromethyl-1H-pyrazole-4-sulfonyl chloride (14.2 mg, 0.06 mmol). The solution was stirred overnight then the solvent evaporated and the residue purified by flash chromatography over silica gel eluting with dichloromethane. Evaporation of solvent under reduced pressure gave the title compound (20 mg). $^1$H NMR (400 MHz, CDCl$_3$): δ 7.51 (s, 1H), 7.21-7.16 (m, 2H), 7.14-7.09 (m, 1H), 7.05-6.95 (m, 2H), 6.93-6.88 (m, 1H), 5.11 (d, 1H), 4.76 (dq, 1H), 3.81 (s, 3H), 3.73 (s, 3H), 1.55 (d, 3H) ppm; MS (ESI) m/z: 498.3 [M+Na]$^+$.

EXAMPLE 31

N-[1-(5'-Chloro-3-fluoro-2'-methoxy-biphenyl-4-yl)-ethyl]-3,4-difluoro-benzenesulfonamide 1-(5'-Chloro-3-fluoro-2'-methoxy-biphenyl-4-yl)-ethylamine was prepared in a similar manner to 1-(2-allyl-5'-fluoro-2'-methoxy-biphenyl-4-yl)-ethylamine (Example 34) using 1-(4-bromo-2-chloro-phenyl)-ethylamine instead of 1-(4-bromo-2-fluoro-phenyl)-ethylamine and 5-chloro-2-methoxyphenyl boronic acid instead of 5-fluoro-2-methoxyphenyl boronic acid. The title compound was prepared in a similar manner to 1-methyl-3-trifluoromethyl-1H-pyrazole-4-sulfonic acid [1-(3,5'-difluoro-2'-methoxy-biphenyl-4-yl)-ethyl]-amide (Example 30) using 1-(5'-chloro-3-fluoro-2'-methoxy-biphenyl-4-yl)-ethylamine and 3,4-di-fluorophenyl sulfonyl chloride instead of 1-methyl-3-trifluoromethyl-1H-pyrazole-4-sulfonyl chloride. $^1$H NMR (400 MHz, CDCl$_3$): δ 7.55-7.41 (m, 2H), 7.28 (q, 1H), 7.17 (d, 1H), 7.12-6.99 (m, 4H), 6.89 (d, 1H), 5.16 (d, 1H), 4.73 (dq, 1H), 3.80 (s, 3H), 1.55 (d, 3H) ppm; MS (ESI) m/z: 478.0 [M+Na]$^+$.

EXAMPLE 32

(R)—N-{1-[4-(2-Chloro-5-fluoro-pyridin-3-yl)-phenyl]-ethyl}-3,4-difluoro-benzenesulfonamide To a solution of (R)-2-[1-(4-bromo-phenyl)-ethyl]-isoindole-1,3-dione (1.19 g, 3.6 mmol) (Example 26) in 1,2-dimethoxyethane (3 ml) was added 2-chloro-5-fluoropyridine-3-boronic acid (0.95 g, 5.4 mmol), tetrakis(triphenylphosphine)palladium (0) (0.21 g, 0.2 mmol) and 2M aqueous sodium carbonate (3.2 ml, 6.4 mmol). The reaction mixture was heated in a microwave oven at 150° C. for 10 min and the solvent evaporated. The residue was partitioned between ethyl acetate and water. The organic phase washed with brine, dried over anhydrous magnesium sulfate and the solvent evaporated. The residue was purified over silica gel eluting with heptane/ethyl acetate to give (R)-2-{1-[4-(2-chloro-5-fluoro-pyridin-3-yl)-phenyl]-ethyl}-isoindole-1,3-dione (0.62 g, 1.6 mmol, 44%) as a clear glass. To a solution of (R)-2-[1-(4-bromo-phenyl)-ethyl]-isoindole-1,3-dione (0.16 g, 0:4 mmol) in methanol (4 ml) was added hydrazine hydrate (0.43 g, 8.6 mmol). The reaction mixture was stirred at room temperature for 18 h and then concentrated under reduced pressure. Dichloromethane was added and the resultant white precipitate filtered off. The solvent was evaporated to give 1-[4-(2-chloro-5-fluoro-pyridin-3-yl)-phenyl]-ethylamine (0.11 g, 0.4 mmol, 100%) as a yellow gum. To a solution of (R)-1-[4-(2-chloro-5-fluoro-pyridin-3-yl)-phenyl]-ethylamine (26 mg, 0.1 mmol) in dichloromethane (1 ml) was added triethylamine (31.6 mg, 0.31 mmol) followed by 3,4-difluorobenzenesulfonyl chloride (28.7 mg, 0.14 mmol). The reaction mixture was agitated for 64 h at room temperature and the solvent evaporated. The crude product was taken up in dimethyl sulfoxide (1 ml) and purified by preparatory LCMS. The solvent was evaporated under reduced pressure to give the title compound (6.7 mg, 0.04 mmol, 38%). $^1$H NMR (400 MHz, DMSO-$d_6$): δ 8.48 (m, 2H), 7.78 (dd, 1H), 7.45-7.60 (m, 3H), 7.27-7.34 (m, 4H), 4.50 (q, 1H), 1.33 (d, 3H) ppm; MS (ESI) m/z: 427 [M+H]$^+$.

EXAMPLE 33

3,5-Dimethyl-isoxazole-4-sulfonic acid [1-(5'-fluoro-2'-methoxy-2-propyl-biphenyl-4-yl)-ethyl]-amide 1-(2-Allyl-5'-fluoro-2'-methoxy-biphenyl-4-yl)-ethanone O-methyl-oxime was prepared in a similar manner to 1-(5'-fluoro-3,2'-dimethoxy-2-propyl-biphenyl-4-yl)-ethanone O-methyl-oxime (Example 35) using 1-(2-allyl-5'-fluoro-2'-methoxy-biphenyl-4-yl)-ethanone instead of 1-(5'-fluoro-3,2'-dimethoxy-2-propyl-biphenyl-4-yl)-ethanone. 1-(5'-Fluoro-2'-methoxy-2-propyl-biphenyl-4-yl)-ethylamine was prepared in a similar manner to 1-(5'-fluoro-3,2'-dimethoxy-2-propyl-biphenyl-4-yl)-ethylamine (Example 35) using 1-(2-allyl-5'-fluoro-2'-methoxy-biphenyl-4-yl)-ethanone O-methyl-oxime instead of 1-(5'-fluoro-3,2'-dimethoxy-2-propyl-biphenyl-4-yl)-ethanone O-methyl-oxime. The title compound was prepared in a similar manner to N-[1-(2-Allyl-5'-fluoro-2'-methoxy-biphenyl-4-yl)-ethyl]-3,4-difluoro-benzenesulfonamide (Example 34) using 1-(5'-fluoro-2'-methoxy-2-propyl-biphenyl-4-yl)-ethylamine and 3,5-dimethyl-isoxazole-4-sulfonyl chloride. MS (ESI) m/z: 447.1 [M+H]$^+$.

EXAMPLE 34

N-[1-(2-Allyl-5'-fluoro-2'-methoxy-biphenyl-4-yl)-ethyl]-3,4-difluoro-benzenesulfonamide A mixture of 3'-allyl-4'-hydroxyacetophenone (0.352 g, 2.0 mmol), N-phenyl-bis(trifluoromethane) sulfonimide) (0.710 g, 2.0 mmol) and potassium carbonate (0.830 g, 6.0 mmol) in tetrahydrofuran (3.0 ml) was heated in a microwave oven at 120° C. for 10 min. The resultant mixture was treated with 5-fluoro-2-methoxyphenyl boronic acid (0.680 g, 0.4 mmol), tetrakis(triphenylphosphine)palladium (0) (0.060 g, 0.05 mmol) and dimethylformamide (1.0 ml) and heated in a microwave oven at 120° C. for 10 min. The mixture was partitioned between ethyl acetate and dilute aqueous sodium carbonate solution. The organic phase was dried over anhydrous sodium sulfate, the solvent evaporated and the residue purified by flash chromatography over silica gel eluting with 9:1 heptane/ethyl acetate. Evaporation of solvent under reduced pressure gave 1-(2-allyl-5'-fluoro-2'-methoxy-biphenyl-4-yl)-ethanone. A solution of 1-(2-allyl-5'-fluoro-2'-methoxy-biphenyl-4-yl)-ethanone (0.319 g, 1.1 mmol), sodium cyanoborohydride (0.140 g, 2.2 mmol) and ammonium acetate (1.7 g, 22 mmol) was stirred under nitrogen at ambient temperature for 72 h, evaporated to dryness under reduced pressure and partitioned between dichloromethane and brine. The organic phase was dried over anhydrous sodium sulfate, the solvent evaporated and the residue purified by flash chromatography over silica gel eluting with 98:2 ethyl acetate/2M ammonia in methanol. Evaporation of solvent under reduced pressure gave 1-(2-allyl-5'-fluoro-2'-methoxy-biphenyl-4-yl)-ethylamine. To a solution of 1-(2-allyl-5'-fluoro-2'-methoxy-biphenyl-4-yl)-ethylamine (19.0 mg, 0.07 mmol) in dichloromethane (1 ml) was added triethylamine (6.7 mg, 0.07 mmol) and 3,4-di-fluorophenyl sulfonyl chloride (14.2 mg, 0.06 mmol). The solution was stirred overnight and the solvent evaporated. The residue was purified by flash chromatography over silica gel eluting with dichloromethane. Evaporation of solvent under reduced pressure gave the title compound. $^1$H NMR (400 MHz, CDCl$_3$): δ 7.52-7.42 (m, 2H), 7.13 (q, 1H), 7.04-6.90 (m, 4H), 6.88-6.83 (m, 1H), 6.77 (q, 1H), 5.67 (dt, 1H), 4.99-4.82 (m, 3H), 4.57 (dq, 1H), 3.71 (s, 3H), 3.09 (br s, 2H), 1.51 (d, 3H) ppm; MS (ESI) m/z: value [M+H]$^+$.

EXAMPLE 35

3,5-Dimethyl-isoxazole-4-sulfonic acid [1-(5'-fluoro-3,2'-dimethoxy-2-propyl-biphenyl-4-yl)-ethyl]-amide 1-(5'-Fluoro-3-hydroxy-2'-methoxy-2-propyl-biphenyl-4-yl)-ethanone was prepared in a similar manner to 1-(2-allyl-5'-fluoro-2'-methoxy-biphenyl-4-yl)-ethanone (Example 34) using 2',4'-dihydroxy-3'-propylacetophenone instead of 3'-allyl-4'-hydroxyacetophenone. A mixture of 1-(5'-fluoro-3-hydroxy-2'-methoxy-2-propyl-biphenyl-4-yl)-ethanone (0.60 g, 2.0 mmol), methyl iodide (0.62 ml, 10.0 mmol) and potassium carbonate (0.83 g, 6.0 mmol) in acetone (20 ml) was refluxed for 6 h. The solvent was evaporated and the residue partitioned between ethyl acetate and dilute aqueous sodium hydroxide solution. The organic phase was washed with water, dried over anhydrous sodium sulfate and the solvent evaporated. The residue was purified by flash chromatography over silica gel eluting with 9:1 heptane/ethyl acetate. Evaporation of solvent under reduced pressure gave 1-(5'-fluoro-3,2'-dimethoxy-2-propyl-biphenyl-4-yl)-ethanone. A solution of 1-(5'-fluoro-3,2'-dimethoxy-2-propyl-biphenyl-4-yl)-ethanone (0.420 g, 1.3 mmol) and methylhydroxylamine hydrochloride (0.125 g, 1.5 mmol) in pyridine (4.0 ml) was left to stand at ambient temperature for 12 h. The solvent was evaporated and the residue partitioned between dichloromethane and water. The organic phase was washed with water, dried over anhydrous sodium sulfate and the solvent evaporated to give 1-(5'-fluoro-3,2'-dimethoxy-2-propyl-biphenyl-4-yl)-ethanone O-methyl-oxime as a mixture of regioisomers. A solution of 1-(5'-fluoro-3,2'-dimethoxy-2-propyl-biphenyl-4-yl)-ethanone O-methyl-oxime (0.450 g 1.3 mmol) in tetrahydrofuran (40 ml), was treated with 1M borane.tetrahydrofuran solution (7.8 ml, 7.8 mmol) and heated under reflux for 2 h. The solution was evaporated to dryness, the residue treated with 2M aqueous hydrochloric acid (30 ml) and the resultant solution was heated under reflux for 3 h, left to cool overnight, washed with dichloromethane, basified with concentrated aqueous sodium hydroxide solution and extracted into dichloromethane. The organic phase was dried over anhydrous sodium sulfate, the solvent evaporated and the residue purified by flash chromatography over silica gel eluting with 98:2 ethyl acetate/2M ammonia in methanol. Evaporation of solvent under reduced pressure gave 1-(5'-fluoro-3,2'-dimethoxy-2-propyl-biphenyl-4-yl)-ethylamine. The title compound was prepared in a similar manner to N-[1-(2-Allyl-5'-fluoro-2'-methoxy-biphenyl-4-yl)-ethyl]-3,4-difluoro-benzenesulfonamide (Example 34) using 1-(5'-fluoro-3,2'-dimethoxy-2-propyl-biphenyl-4-yl)-ethylamine and 3,5-dimethyl-isoxazole-4-sulfonyl chloride. MS (ESI) m/z: 477.1 [M+H]$^+$.

EXAMPLE 36

(R)-1-Methyl-3-trifluoromethyl-1H-pyrazole-4-sulfonic acid [1-(5'-chloro-2'-methoxy-biphenyl-4-yl)-ethyl]-amide Prepared in a similar manner to (R)-1-Methyl-3-trifluoromethyl-1H-pyrazole-4-sulfonic acid 1-{[4-(5-chloro-2-methoxypyridin-3-yl)-phenyl]-ethyl}-amide (Example 39) using (R)-1-(5'-chloro-2'-methoxy-biphenyl-4-yl)-ethylamine instead of (R)-1-[4-(5-chloro-2-methoxy-pyridin-3-yl)-phenyl]-ethylamine. Title compound: $^1$H NMR (400 MHz, CDCl$_3$): δ 7.44-7.14 (m, 7H), 6.90 (d, 1H), 4.96 (d, 1H), 4.60 (dq, 1H), 3.81 (s, 3H), 3.72 (s, 3H), 1.51 (d, 3H) ppm; MS (ESI) m/z: value [M+H]$^+$.

EXAMPLE 37

1-Methyl-3-trifluoromethyl-1H-pyrazole-4-sulfonic acid {1-[4-(5-fluoro-2-methoxy-pyridin-3-yl)-phenyl]-ethyl}-amide A mixture of 3-bromo-5-fluoro-2-methoxy-pyridine (1.0 g, 4.9 mmol), 4-acetylphenylboronic acid (1.59 g, 9.7 mmol), tetrakis(triphenylphosphine)palladium (0) (0.28 g, 0.24 mmol), 2M aqueous sodium carbonate solution (2.4 ml) and 1,2-dimethoxyethane (5 ml) was heated in a microwave oven at 150° C. for 20 min. The solvent was evaporated and the residue partitioned between ethyl acetate and water. The organic phase was washed with water, brine and dried over anhydrous magnesium sulfate. The solvent was evaporated and the residue chromatographed on silica gel eluting with 3:1 heptane/ethyl acetate to give 1-[4-(5-fluoro-2-methoxy-pyridin-3-yl)-phenyl]-ethanone (1.0 g, 4.0 mmol, 82%). 1-[4-(5-fluoro-2-methoxy-pyridin-3-yl)-phenyl]-ethanone (1.0 g, 4.1 mmol) was treated with sodium borohydride (4.0 eq) in tetrahydrofuran and dichloromethane at room temperature. The solvent was evaporated to give 1-[4-(5-fluoro-2-methoxy-pyridin-3-yl)-phenyl]-ethanol (0.51 g, 2.1 mmol, 51%). To a solution 1-[4-(5-fluoro-2-methoxy-pyridin-3-yl)-phenyl]-ethanol (0.5 g, 2.0 mmol) in tetrahydrofuran (5 ml) was added triphenylphosphine (0.63 g, 2.4 mmol) and pthalimide (0.35 g, 2.4 mmol). The reaction was cooled to below 5° C. before adding diethylazodicarboxylate (0.42 g, 2.4 mmol) in a dropwise manner maintaining the temperature below 5° C. The reaction mixture was stirred for 24 h at room temperature. The solvent was evaporated and the residue partitioned between ethyl acetate and water.

The organic phase was washed with water, brine and dried over anhydrous magnesium sulfate. The solvent was evaporated and the residue chromatographed on silica gel to give to give 2-{1-[4-(5-fluoro-2-methoxy-pyridin-3-yl)-phenyl]-ethyl}-isoindole-1,3-dione (0.31 g, 0.82 mmol, 41%). To a solution of 2-{1-[4-(5-fluoro-2-methoxy-pyridin-3-yl)-phenyl]-ethyl}-isoindole-1,3-dione (0.31 g, 0.8 mmol) in dioxan/methanol (1:1, 10 ml) was added hydrazine hydrate (0.83 g, 46.5 mmol). The reaction was stirred at room temperature for 24 h. The solvent was evaporated and dichloromethane added. The resultant white solid was filtered off and dried to give 1-[4-(5-fluoro-2-methoxy-pyridin-3-yl)-phenyl]-ethylamine (0.21 g, 0.8 mmol, 100%) as a clear oil. To a solution of 1-[4-(5-fluoro-2-methoxy-pyridin-3-yl)-phenyl]-ethylamine (0.1 g, 0.4 mmol) in dichloromethane (2 ml) was added triethylamine (123 mg, 1.2 mmol) and 1-methyl-3-(trifluoromethyl)-1H-pyrazole-4-sulfonylchloride (111 mg, 0.45 mmol). The reaction mixture was agitated for 16 h and quenched with saturated aqueuos sodium bicarbonate solution. The organic phase was washed with water, brine and dried over anhydrous magneium sulfate. The residue was chromatographed on silica gel to give the title compound (42 mg, 0.1 mmol, 25%). $^1$H NMR (400 MHz, CDCl$_3$): δ 8.00 (d, 1H), 7.45 (m, 3H), 7.35 (dd, 1H), 7.21 (d, 2H), 4.86 (d, 1H), 4.60 (q, 1H), 3.96 (s, 3H), 3.75 (s, 3H), 1.50 (b, 3H) ppm; MS (ESI) m/z: 459.3 [M+H]$^+$.

EXAMPLE 38

1-Methyl-3-trifluoromethyl-1H-pyrazole-4-sulfonic acid 4-(5-chloro-2-methoxy-pyridin-3-yl)-3-trifluoromethoxy-benzylamide To 4-hydroxy-3-trifluoromethoxy-benzylaldehyde (1.0 g, 4.85 mmol) in dry pyridine (4 ml) at 0° C. was slowly added trifluoromethane sulfonic anhydride maintaining the reaction temperature at 0° C. The mixture was allowed to warm to ambient temperature and left to stir for 1 h. The reaction mixture was quenched with water (50 ml) and extracted with ethyl acetate. The combined extracts were washed with 2M hydrochloric acid, water and dried over anhydrous magnesium sulfate. The solvent was evaporated to give trifluoromethanesulfonic acid-4-formyl-2-trifluoromethoxy-phenyl ester (1.3 g, 3.85 mmol) as a brown oil. (±)-Tert-butylsulfinamine (0.311 g, 2.57 mmol) and titanium tetraethoxide (1.07 g, 4.69 mmol) were added to a solution of trifluoro-methanesulfonicacid-4-formyl-2-trifluoromethoxy-phenylester (0.791 g, 2.34 mmol) in dry tetrahydrofuran (20 ml) and the mixture stirred under nitrogen atmosphere at ambient temperature for 18 h. The reaction mixture was slowly added to a suspension of sodium borohyride (0.356 g, 9.4 mmol) in tetrahydrofuran at –50° C. and then allowed to warm to ambient temperature and left to stir for 1 h. The mixture was quenched with brine (50 ml) and ethyl acetate (50 ml) added. This mixture was filtered through a bed of dicalite and washed with copious amounts of water and ethyl acetate. The filtrate was phase separated, the organic phase dried over anhydrous magnesium sulfate and the solvent evaporated. Methanol (5 ml) was added to the residue and the mixture was poured onto an SCX column, washed with methanol and then eluted with 3M ammonia in methanol solution. The solvent was evaporated and the residue dissolved in 3M hydrogen chloride in diethyl ether solution. The solvent was evaporated to give trifluoro-methanesulfonicacid-4-aminomethyl-2-trifluoromethoxy-phenyl ester hydrochloride (0.184 g, 0.49 mmol) as a colourless solid. Trifluoro-methanesulfonicacid-4-aminomethyl-2-trifluoromethoxy-phenyl ester hydrochloride (0.184 g, 0.49 mmol) was suspended in dry tetrahydrofuran (3 ml). Di-tert-butyldicarbonate (0.108 g, 0.495 mmol) and triethylamine (0.198 g, 1.96 mmol) were added and the mixture stirred at ambient temperature for 2 h. The solvent was evaporated and the residue partitioned between water (10 ml) and ethyl acetate (10 ml). The organics phase was dried over anhydrous magnesium sulfate and the solvent evaporated to give trifluoro-methanesulfonicacid-4-(tert-butoxycarbonylaminomethyl)-2-trifluoromethoxy-phenyl ester (0.176 g, 0.407 mmol) as pale yellow oil. A mixture of trifluoro-methanesulfonicacid-4-(tert-butoxycarbonylaminomethyl)-2-trifluoromethoxy-phenyl ester (0.176 g, 0.407 mmol), 5-chloro-2-methoxypyridine boronic acid (0.151 g, 0.805 mmol), toluene (1 ml), ethanol (1 ml), 2M aqueous sodium carbonate solution (2 ml) and tetrakis(triphenylphosphine) palladium (0) was heated in a microwave oven at 120° C. for 15 min. The reaction mixture was quenched with brine and extracted with ethyl acetate. The combined extracts were filtered through dicalite and the filtrate dried over anhydrous magnesium sulfate. The solvent was evaporated and the residue chromatographed on silica gel eluting with 6:40% heptane/ethyl acetate to give [4-(5-chloro-2-methoxypyridin-3-yl)-3-trifluoromethoxy-benzyl]-carbamic acid-tert-butyl ester (0.0745 g, 0.172 mmol) as a colourless solid. [4-(5-Chloro-2-methoxypyridin-3-yl)-3-trifluoromethoxy-benzyl]-carbamic acid-tert-butyl ester (0.0745 g, 0.172 mmol) was dissolved in dichloromethane (1 ml). Trifluoroacetic acid (1.485 g, 13 mmol) added and the solution stirred for 2 h at ambient temperature. The solvent was evaporated, the residue dissolved in methanol and then poured onto an SCX column. The column was washed with methanol and then eluted with ammonia in methanol solution. The solvent was evaporated to give 4-(5-chloro-2-methoxypyridin-3-yl)-3-trifluoromethoxy-benzylamine (0.045 g, 0.136 mmol) as oil. 1-Methyl-3-trifluoromethyl-1H-pyrazole-4-sulfonyl chloride (0.0302 g, 0.122 mmol) and triethylamine (0.038 g, 0.384 mmol) were added to a solution of 4-(5-chloro-2-methoxy-pyridin-3-yl)-3-trifluoromethoxy-benzylamine (0.042 g, 0.128 mmol) in dry dichloromethane (1 ml) and the mixture stirred at ambient temperature for 18 h. The solvent was evaporated and the residue chromatographed on silica gel eluting with 4:6 heptane/ethyl acetate to give the title compound (0.039 g, 0.072 mmol) as a clear solid. MS (ESI) m/z: 545 [M+H]$^+$.

EXAMPLE 39

(R)-1-Methyl-3-trifluoromethyl-1H-pyrazole-4-sulfonic acid 1-{[4-(5-chloro-2-methoxypyridin-3-yl)-phenyl]-ethyl}-amide Palladium Acetate (30 mg, 0.134 mmol) was added to a mixture of (5-chloro-2-methoxy)pyrid-3-yl-boronic acid (500 mg, 2.67 mmol) and (R)-1-(4-bromophenyl)ethylamine (266 mg, 1.33 mmol) in water (20 ml). This mixture was heated in the microwave oven at 180° C. for 7 min, diluted with methanol (200 ml) and added to a SCX column eluting with 2M ammonia in methanol. The solvent was evaporated to give (R)-1-[4-(5-chloro-2-methoxy-pyridin-3-yl)-phenyl]-ethylamine (395 mg, 1.50 mmol, 113.2%) as an oil.

To a suspension of (R)-1-(4-bromophenyl)ethylamine (23.89 g, 0.101 mol) in tetrahydrofuran (200 ml) was added triethylamine (21 ml), 4-dimethylaminopyridine (1.5 g) and di-tert-butyldicarbonate (26.5 g, 0.121 mol). The solution was stirred overnight then diluted with diethyl ether and washed with 2M aqueous hydrogen chloride solution, 10% aqueous sodium carbonate solution and brine. The organic phase was dried over anhydrous sodium sulfate and the solution concentrated to low volume. Heptane was added and the resulting white solid filtered off and dried to give (R)-[1-(4-bromophenyl)-ethyl]-carbamic acid tert-butyl ester (17 g). To a solution of (R)-[1-(4-bromophenyl)-ethyl]-carbamic acid tert-butyl ester (2 g, 6.7 mmol) in toluene (40 ml) was added 5-chloro-2-methoxypyridine boronic acid (2.5 g, 13.3 mmol), 2M aqueous sodium carbonate solution (6.8 ml) and tetrakis (triphenylphosphine) palladium (0) (0.4 g). The solution was heated under reflux for 48 h then washed with water, brine and dried over anhydrous sodium sulfate. The solvent was evaporated and the residue dissolved in dichloromethane (50 ml) and the solution cooled to 0° C. Trifluoroacetic acid (20 ml) was added and the solution stirred for 3 h then evaporated to a gum which was chromatographed on a SCX column eluting with methanol then ammonia/methanol. The solvent was removed and the residue flash chromatographed on silica eluting with 9:1 dichloromethane/methanol then 9:1 dichloromethane/methanol-ammonia. The solvent was evaporated to give (R)-1-[4-(5-chloro-2-methoxy-pyridin-3-yl)-phenyl]-ethylamine (1.37 g) as a gum.

To a solution of (R)-1-[4-(5-chloro-2-methoxypyridin-3-yl)-phenyl]ethylamine (1.15 g, 4.4 mmol) in dichloromethane (10 ml) was added triethylamine 1.25 ml) and 1-methyl-3-trifluoromethyl-1H-pyrazole-4-sulfonyl chloride (1 g). The solution was stirred overnight then diluted with dichloromethane and washed with 2M aqueous hydrogen chloride solution, 5% aqueous sodium carbonate solution and dried over anhydrous magnesium sulfate. The solvent was evaporated and the residue flash chromatographed on silica eluting with ethyl acetate then 9:1 dichloromethane-methanol. The solvent was evaporated and the residue crystallized from heptane-ethyl actetate to give the title compound. $^1$H NMR (400 MHz, CDCl$_3$): δ 8.10 (s, 1H), 7.56 (s, 1H), 7.43, 7.22 (a/b, 4H), 4.88 (d, 1H), 4.60 (m, 1H), 3.96 (s, 3H), 3.75 (s, 3H), 1.51 (d, 3H) ppm; MS (ESI) m/z: 475.1 [M+H]$^+$.

EXAMPLE 40

(R)-1-Methyl-3-trifluoromethyl-1H-pyrazole-4-sulfonic acid {1-[4-(5-chloro-2-methoxy-pyridin-3-yl)-2-methoxy-phenyl]-ethyl}-amide A mixture of 4-bromo-2-hydroxyacetophenone (0.460 g, 2.0 mmol), titanium tetraethoxide (1.0 g, 4.0 mmol) and (R)-2-methyl-2-propanesulfinamide (0.266 g, 2.2 mmol) in dichloromethane (3.0 ml) was heated in a microwave oven at 120° C. for 15 min. The mixture was cooled in ice and added to a stirred mixture of sodium borohydride (0.30 g, 8.0 mmol) in tetrahydrofuran (50 ml). This mixture was stirred for 1 h at ambient temperature, treated with brine (30 ml) and extracted with ethyl acetate. The combined organic extracts were washed with brine, dried over anhydrous sodium sulfate and the solvent evaporated The residue was flash chromatographed on silica gel eluting with 3:1 heptane/ethyl acetate to give (R)-2-methyl-propane-2-sulfinic acid [1-(4-bromo-2-methoxy-phenyl)-ethyl]-amide. A mixture of (R)-2-methyl-propane-2-sulfinic acid [1-(4-bromo-2-methoxy-phenyl)-ethyl]-amide (0.130 g, 0.4 mmol), 5-chloro-2-methoxy-pyridine-3-boronic acid (0.150 g, 0.8 mmol), tetrakis (triphenylphosphine)palladium (0) (0.025 g, 0.02 mmol), 2M aqueous sodium carbonate solution (2 ml), toluene (1 ml) and ethanol (1 ml) was heated in a microwave oven at 120° C. for 15 min. The mixture was partitioned between ethyl acetate and dilute aqueous sodium carbonate solution. The organic layer was dried over anhydrous sodium sulfate, the solvent evaporated and the residue dissolved in methanol. This solution was treated with 2M hydrogen chloride in diethyl ether solution. After standing for 2 hours, the mixture was poured onto an SCX column, washed with methanol and then eluted with 1M ammonia in methanol solution. The solvent was evaporated and the residue flash chromatographed on silica gel eluting with 98:2 ethyl acetate/2M ammonia in methanol to give (R)-1-[4-(5-chloro-2-methoxy-pyridin-3-yl)-2-methoxy-phenyl]-ethylamine. The title compound was prepared in a similar manner to 1-methyl-3-trifluoromethyl-1H-pyrazole-4-sulfonic acid [1-(3,5'-difluoro-2'-methoxy-biphenyl-4-yl)-ethyl]-amide (Example 30) using (R)-1-[4-(5-chloro-2-methoxy-pyridin-3-yl)-2-methoxy-phenyl]-ethylamine instead of 1-(3,5'-difluoro-2'-methoxy-biphenyl-4-yl)-ethylamine. MS (ESI) m/z: 505.0 [M+H]$^+$.

EXAMPLE 41

5-Chloro-1,3-dimethyl-1H-pyrazole-4-sulfonic acid (5'-chloro-3,2'-dimethoxy-biphenyl-4-ylmethyl)-amide A mixture of 2-methoxy-4-hydroxybenzaldehyde (0.406 g, 2.67 mmol), N-phenyl-bis (trifluoromethane)sulfonimide) (0.953 g, 2.67 mmol) and potassium carbonate (0.74 g, 5.3 mmol) in tetrahydrofuran (4.0 ml) was heated in a microwave oven at 120° C. for 10 min. The mixture was partitioned between ethyl acetate and dilute aqueous sodium hydroxide solution. The organic phase was washed with water, dried over anhydrous sodium sulfate and the solvent evaporated to give trifluoro-methanesulfonic acid 4-formyl-3-methoxy-phenyl ester. A mixture of trifluoro-methanesulfonic acid 4-formyl-3-methoxy-phenyl ester (5.05 g, 17.8 mmol), titanium tetraethoxide (8.3 ml, 40.0 mmol) and 2-methyl-2-propanesulfinamide (4.74 g, 39.1 mmol) in tetrahydrofuran (50 ml) was stirred at ambient temperature for 2 days. The mixture was cooled in ice and then added portionwise to a stirred mixture of sodium borohydride (2.70 g, 71.1 mmol) in tetrahydrofuran (25 ml) at −78° C. The solution was allowed to warm to ambient temperature, treated slowly with water (with cooling) and extracted with ethyl acetate. The combined organic extracts were washed brine, dried over anhydrous sodium sulfate and the solvent evaporated. The residue was flash chromatographed on silica gel (gradient elution with 1:1 heptane/ethyl acetate to 100% ethyl acetate to give trifluoro-methanesulfonic acid 3-methoxy-4-[(2-methyl-propane-2-sulfinylamino)-methyl]-phenyl ester. A mixture of trifluoro-methanesulfonic acid 3-methoxy-4-[(2-methyl-propane-2-sulfinylamino)-methyl]-phenyl ester (0.10 g, 0.26 mmol), 5-chloro-2-methoxyphenyl boronic acid (0.053 g, 0.28 mmol), tetrakis(triphenylphosphine)palladium (0) (7.4 mg, 0.006 mmol) and potassium carbonate (0.071 g, 0.52 mmol) in toluene (0.8 ml) and methanol (0.2 ml) was heated in a microwave oven at 120° C. for 15 min. The mixture was partitioned between ethyl acetate and dilute aqueous sodium hydroxide solution. The organic phase was dried over anhyrous sodium sulfate, the solvent evaporated and the residue flash chromatographed on silica gel eluting with 1:1 heptane/ethyl acetate. The solvent was evaporated and the residue dissolved in ethanol, and treated with 2M hydrogen chloride in diethyl ether solution. After standing for 2 h, the mixture was poured onto an SCX column, washed with methanol and then eluted with 1M ammonia in methanol solution. The solvent was evaporated and the residue flash chromatographed on silica gel eluting with 98:2 ethyl acetate/2M ammonia in methanol solution to give (5'-chloro-3,2'-dimethoxy-biphenyl-4-yl)-methylamine. To a solution of (5'-chloro-3,2'-dimethoxy-biphenyl-4-yl)-methylamine (0.011 g, 0.04 mmol) in dichloromethane (1 ml) was added triethylamine (4.0 mg, 0.04 mmol) and 5-chloro-1,3-dimethyl-1h-pyrazole-4-sulfonyl chloride (9.2 mg, 0.04 mmol) and the solution was stirred overnight. Purification by preparatory LCMS and removal of solvent under reduced pressure gave the title compound. MS (ESI) m/z: 471.0 [M+H]$^+$.

EXAMPLE 42

3,5-Dimethyl-isoxazole-4-sulfonic acid 4-(5-chloro-2-methoxy-pyridin-3-yl)-3-methoxy-benzylamide A mixture of 3-methoxy-4-hydroxybenzaldehyde (0.406 g, 2.67 mmol), N-phenyl-bis (trifluoromethane)sulfonimide) (0.953 g, 2.67 mmol) and potassium carbonate (0.74 g, 5.3 mmol) in tetrahydrofuran (4.0 ml) was heated in a microwave oven at 120° C. for 10 min. The mixture was partitioned between ethyl acetate and dilute aqueous sodium hydroxide solution. The organic phase was washed with water, dried over anhydrous sodium sulfate and the solvent evaporated to give the trifluoro-methanesulfonic acid 4-formyl-2-methoxy-phenyl ester. A mixture of trifluoro-methanesulfonic acid 4-formyl-2-methoxy-phenyl ester (1.00 g, 3.52 mmol), titanium tetraethoxide (1.61 g, 7.04 mmol) and 2-methyl-2-propanesulfinamide (0.94 g, 7.75 mmol) in tetrahydrofuran (10 ml) was heated under reflux for 2 h, and then stirred at ambient temperature overnight. Further titanium tetraethoxide (0.80 g, 3.52 mmol) was added and the mixture stirred at ambient temperature overnight. The mixture was cooled in ice and then added portionwise to a stirred mixture of sodium borohydride (0.53 g, 14.1 mmol) in tetrahydrofuran (10 ml) at −78° C. The solution was allowed to warm to ambient temperature, treated slowly with water (with cooling) and extracted with ethyl acetate. The combined organic extracts were washed brine, dried over anhydrous sodium sulfate and the solvent evaporated. The residue was dissolved in methanol (10 ml), and treated with 2M hydrogen chloride in diethyl ether solution (5 ml). After standing for 2 hours, the solvent was evaporated, the residue triturated with diethyl ether, and the solid filtered and dried to give trifluoro-methanesulfonic acid 4-aminomethyl-2-methoxy-phenyl ester hydrochloride. A stirred solution of trifluoro-methanesulfonic acid 4-aminomethyl-2-methoxy-phenyl ester hydrochloride (0.37 g, 1.29 mmol) and triethylamine (0.4 ml, 2.7 mmol) in dichloromethane (10 ml) was treated with di-tert-butyl dicarbonate (0.28 g, 1.29 mmol) and stirred at ambient temperature overnight. The solvent was evaporated and the residue partitioned between ethyl acetate and water. The organic phase was washed with water, dried over anhydrous sodium sulfate and the solvent evaporated to give trifluoro-methanesulfonic acid 4-(tert-butoxycarbonylamino-methyl)-2-methoxy-phenyl ester. A mixture of trifluoro-methanesulfonic acid 4-(tert-butoxycarbonylamino-methyl)-2-methoxy-phenyl ester (0.20 g, 0.52 mmol), 5-chloro-2-methoxy-pyridine-3-boronic acid (0.19 g, 1.0 mmol), tetrakis(triphenylphosphine) palladium (0) (0.073 g, 0.06 mmol), 2M aqueous sodium carbonate solution (2 ml), toluene (1 ml) and ethanol (1 ml) was heated in a microwave oven at 120° C. for 15 min. The mixture was partitioned between ethyl acetate and dilute aqueous sodium hydroxide solution. The organic phase was dried over anhyrous sodium sulfate, the solvent evaporated and the residue flash chromatographed over silica gel eluting with 1:1 heptane/ethyl acetate eluant to give the [4-(5-chloro-2-methoxy-pyridin-3-yl)-3-methoxy-benzyl]-carbamic acid tert-butyl ester. A solution of [4-(5-chloro-2-methoxy-pyridin-3-yl)-3-methoxy-benzyl]-carbamic acid tert-butyl ester (0.15 g, 0.4 mmol) in dichloromethane (10 ml) was treated with trifluoromethylacetic acid (0.5 ml), stirred at ambient temperature overnight, and the solvent evaporated to give 4-(5-chloro-2-methoxy-pyridin-3-yl)-3-methoxy-benzylamine trifluoromethyl acetate. The title compound was prepared in a similar manner to 5-chloro-1,3-dimethyl-1H-pyrazole-4-sulfonic acid (5'-chloro-3,2'-dimethoxy-biphenyl-4-ylmethyl)-amide (Example 41) using 4-(5-chloro-2-methoxy-pyridin-3-yl)-3-methoxy-benzylamine trifluoromethyl acetate instead of (5'-chloro-3,2'-dimethoxy-biphenyl-4-yl)-methylamine and 3,5-dimethylisoxazole-4-sulfonyl chloride instead of 5-chloro-1,3-dimethyl-1h-pyrazole-4-sulfonyl chloride. MS (ESI) m/z: 438.1 [M+H]$^+$.

EXAMPLE 43

(R)-5-Chloro-1,3-dimethyl-1H-pyrazole-4-sulfonic acid {1-[3-benzyloxy-4-(2-methoxy-pyridin-3-yl)-phenyl]-ethyl}-amide To a stirred solution of (R)-[1-(3-hydroxy-phenyl)-ethyl] carbamic acid tert-butyl ester 47.05 g, 201 mmol) in acetonitrile (1000 ml) cooled to −78° C. was added sodium iodide (18.1 g, 121 mmol). Reaction mixture was stirred for 5 min followed by addition of [N-chloro-p-toluenesulfonamide sodium salt trihydrate] (33.98 g, 121 mmol) stirring for a further 15 min. Reaction mixture was then filtered and washed with acetonitrile. The solvent was evaporated and the residue flash chromatographed on silica gel eluting with 3:1 heptane/ethyl acetate to give (R)-[1-(3-Hydroxy-4-iodo-phenyl)-ethyl]-carbamic acid tert-butyl ester (51 g). To a stirred solution of (R)-[1-(3-hydroxy-4-iodo-phenyl)-ethyl]-carbamic acid tert-butyl ester (0.873 g, 2.4 mmol) and potassium carbonate (0.4 g, 2.89 mmol) in acetone (20 ml) was added benzyl bromide (0.31 ml, 2.65 mmol). The reaction mixture was stirred for 7 h at ambient temperature. The solvent was evaporated and the residue flash chromatographed on silica gel eluting with 9:1 petroleum ether/ethyl acetate to give (R)-[1-(3-benzyloxy-4-iodo-phenyl)-ethyl]-carbamic acid tert-butyl ester (0.630 g). To a stirred solution of (R)-[1-(3-benzyloxy-4-iodo-phenyl)-ethyl]-carbamic acid tert-butyl ester (0.5 g, 1.1 mmol) in toluene (30 ml) and ethanol (ml) was added 2-methoxypyridine-3-boronic acid (0.340 g, 2.2 mmol), 2M aqueous sodium carbonate solution (2 ml, 4.4 mmol) and tetrakis(triphenylphoshpine)palladium (0.140 g, 0.11 mmol). The mixture was heated under reflux for 16 h and the solvent evaporated. The residue was dissolved in dichloromethane and washed with saturated aqueous sodium bicarbonate solution. The solvent was evaporated and the residue flash chromatographed on silica gel eluting with 5:1 heptane/ethyl acetate to give (R)-(1-[3-benzyloxy-4-(2-methoxy-pyridin-3-yl)-phenyl]-ethyl)-carbamic acid tert-butyl ester (0.450 g) as yellow solid. To a stirred solution of (R)-(1-[3-benzyloxy-4-(2-methoxy-pyridin-3-yl)-phenyl]-ethyl)-carbamic acid tert-butyl ester (0.450 g, 1.04 mmol) in dichloromethane (10 ml) was added trifluoroacetic acid (3 ml): The mixture was stirred at ambient temperature for 16 h, and then partitioned between dichloromethane and 4M aqueous sodium hydroxide solution. The organic phase was dried over anhydrous sodium sulfate and the solvent evaporated. The residue was purified on a SCX column (eluted with 1:1 dichloromethane/methanol then with 2M ammonia in methanol) to give (R)-1-[3-benzyloxy-4-(2-methoxy-pyridin-3-yl)-phenyl]-ethylamine (0.3 g) as a gum. The title compound was prepared in a similar manner to N-(5'-fluoro-2,2'-dimethoxy-biphenyl-4-ylmethyl)-4-methoxy-benzenesulfonamide (Example 6) using (R)-1-[3-benzyloxy-4-(2-methoxy-pyridin-3-yl)-phenyl]-ethylamine and 5-chloro-1,3-dimethyl-1H-pyrazole-4-sulfonyl chloride. MS (ESI) m/z: 527.0 [M+H]⁺.

EXAMPLE 44

(R)-5-Chloro-1,3-dimethyl-1H-pyrazole-4-sulfonic acid {1-[4-(5-chloro-2-ethoxy-pyridin-3-yl)-phenyl]-ethyl}-amide To a solution of 2,5-dichloropyridine (7.0 g, 0.047 mol) in ethanol (44.5 ml) was slowly added a 25% solution of sodium ethoxide in ethanol (13.6 ml, 50 mmol). The reaction mixture was heated to 150° C. for 10 min in a microwave oven. The solvent was evaporated and the residue partitioned between diethyl ether and water. The organic phase was washed with water, brine and dried over anhydrous potassium carbonate. The solvent was evaporated under reduced pressure to give 5-chloro-2-ethoxy-pyridine (4.13 g, 26.2 mmol, 56%). To a solution of sodium acetate (4.91 g, 60 mmol) in acetic acid (10 ml) at 0-5° C. was added a solution of 5-chloro-2-ethoxy-pyridine (9.40 g, 60 mmol) in acetic acid (10 ml) under nitrogen atmosphere. A solution of bromine (19.2 g, 0.12 mmol) in acetic acid (20 ml) was added dropwise and the mixture heated under reflux for 16 h. The mixture was partitioned between diethyl ether and water. The organic phase was washed with 4M sodium hydroxide (200 ml), then with 5% aqueous sodium thiosulphate and dried over anhydrous potassium carbonate The solvent was evaporated to give 3-bromo-5-chloro-2-ethoxy-pyridine (11.6 g, 49 mmol, 82%). A mixture of 3-bromo-5-chloro-2-ethoxy-pyridine (3.47 g, 15 mmol), 4-acetylphenylboronic acid (7.19 g, 44 mmol), tetrakis(triphenylphosphine)palladium (0) (0.87 g, 0.75 mmol), 2M aqueous sodium carbonate (22 ml) and 1,2-dimethoxyethane (57 ml) was refluxed under nitrogen atmosphere for 64 h. The reaction mixture was concentrated under reduced pressure and partitioned between ethyl acetate and water. The organic phase was washed with water, brine and dried over anhydrous magnesium sulfate. The solvent was evaporated and the residue chromatographed on silica gel. The solvent was evaporated to give 1-[4-(5-chloro-2-ethoxy-pyridin-3-yl)-phenyl]-ethanone (2.68 g, 9.7 mmol, 65%). To a solution of (R)-tert-butane sulfinamide (0.48 g, 4.0 mmol) in tetrahydrofuran (20 ml) under argon atmosphere was added 1-[4-(5-chloro-2-ethoxy-pyridin-3-yl)-phenyl]-ethanone (1.0 g, 3.6 mmol) and titanium tetraethoxide (1.66 g, 7.3 mmol). The mixture was heated under reflux for 48. The reaction mixture was cooled to −50° C. then sodium borohydride (0.55 g, 14.5 mmol) in tetrahydrofuran (10 ml) was added by cannula. Cooling was removed and the reaction mixture warmed to room temperature over 2 h. The reaction was quenched by addition of methanol (5 ml) and the mixture added to brine and filtered through Celite. The mixture was concentrated and partitioned between ethyl acetate and water. The organic phase was washed with water, brine and dried over anhydrous magnesium sulfate. The solvent was evaporated and the residue chromatographed on silica gel. The solvent was evaporated to give (R)-2-methyl-propane-2-sulfinic acid {1-[4-(5-chloro-2-ethoxy-pyridin-3-yl)-phenyl]-ethyl}-amide (0.39 g, 1.0 mmol, 28%). To a solution of (R)-2-methyl-propane-2-sulfinic acid {1-[4-(5-chloro-2-ethoxy-pyridin-3-yl)-phenyl]-ethyl}-amide (1.18 g, 3.1 mmol) in methanol (6.2 ml) was added 1 M Hydrogen chloride in diethyl ether (6.2 ml). The reaction was stirred at room temperature for 1 h and the solvent evaporated. The residue was added to a SCX column (eluted with 2M ammonia in methanol) and further purified by chromatography over silica gel eluting with 3:1 heptane/ethyl acetate). Evaporation of solvent under reduced pressure gave (R)-1-[4-(5-chloro-2-ethoxy-pyridin-3-yl)-phenyl]-ethylamine (385 mg, 1.4 mmol, 45%). To a solution of (R)-1-[4-(5-chloro-2-ethoxy-pyridin-3-yl)-phenyl]-ethylamine (128 mg, 0.46 mmol) in dichloromethane (2 ml) was added triethylamine (140 mg, 1.4 mmol) and 5-chloro-1,3-dimethyl-1H-pyrazole-4-sulfonyl chloride (127 mg, 0.55 mmol). The reaction was agitated at room temperature for 16 h and quenched with saturated aqueous sodium bicarbonate solution. The organic phase was dried over anhydrous magnesium sulfate and the solvent evaporated. The residue was chromatographed over silica gel and the solvent evaporated to give the title compound (51 mg, 0.1 mmol, 22%). $^1$H NMR (400 MHz, DMSO-d$_6$): δ 8.36 (d, 1H), 8.19 (d, 1H), 7.77 (d, 1H), 7.46 (d, 2H), 7.26 (d, 2H), 4.36 (m, 3H), 3.53 (s, 3H), 2.22 (s, 3H), 1.33 (m, 6H) ppm; MS (ESI) m/z: 469.1 [M+H]⁺.

EXAMPLE 45

3,5-Dimethyl-isoxazole-4-sulfonic acid [1-(5'-fluoro-2-hydroxymethyl-2'-methoxy-biphenyl-4-yl)-ethyl]-amide 4-Acetyl-5'-fluoro-2'-methoxy-biphenyl-2-carboxylic acid methyl ester was prepared in a similar manner to 1-(2-allyl-5'-fluoro-2'-methoxy-biphenyl-4-yl)-ethanone (Example 34) using methyl 5-acetylsalicylate instead of 3'-allyl-4'-hydroxyacetophenone. 5'-Fluoro-2'-methoxy-4-(1-methoxyimino-ethyl)-biphenyl-2-carboxylic acid methyl ester was prepared in a similar manner to 1-(5'-fluoro-3,2'-dimethoxy-2-propyl-biphenyl-4-yl)-ethanone O-methyl-oxime (Example 35) using 4-acetyl-5'-fluoro-2'-methoxy-biphenyl-2-carboxylic acid methyl ester instead of 1-(5'-fluoro-3,2'-dimethoxy-2-propyl-biphenyl-4-yl)-ethanone. A solution of 5'-fluoro-2'-methoxy-4-(1-methoxyimino-ethyl)-biphenyl-2-carboxylic acid methyl ester (3.61 g, 10 mmol) in tetrahydrofuran (40 ml), was treated dropwise with 1M borane.tetrahydrofuran solution (50 ml, 50 mmol) with ice cooling, and the resultant solution was stirred at ambient temperature for 3 days. The solvent was evaporated and the residue was partitioned between dichloromethane and dilute aqueous sodium carbonate solution. The organic phase was washed with water, the solvent evaporated and the residue treated with ethanol (50 ml), caesium fluoride (4.05 g) and sodium carbonate (4.05 g). This mixture was heated under reflux overnight and the solvent evaporated. The residue was treated with water and extracted with dichloromethane. The organic extracts were dried over anhydruous sodium sulfate, the solvent evaporated and the residue flash chromatographed over silica gel uluting with 98:2 ethyl acetate/2M ammonia in methanol to give 4-(1-amino-ethyl)-5'-fluoro-2'-methoxy-biphenyl-2-carboxylic acid ethyl ester. 4-[1-(3,5-Dimethyl-isoxazole-4-sulfonylamino)-ethyl]-5'-fluoro-2'-methoxy-biphenyl-2-carboxylic acid ethyl ester was prepared in a similar manner to N-[1-(2-allyl-5'-fluoro-2'-methoxy-biphenyl-4-yl)-ethyl]-3,4-difluoro-benzenesulfonamide (Example 34) using 4-(1-amino-ethyl)-5'-fluoro-2'-methoxy-biphenyl-2-carboxylic acid ethyl ester and 3,5-dimethyl-isoxazole-4-sulfonyl chloride. A solution of 4-[1-(3,5-dimethyl-isoxazole-4-sulfonylamino)-ethyl]-5'-fluoro-2'-methoxy-biphenyl-2-carboxylic acid ethyl ester (0.13 g, 0.28 mmol) in tetrahydrofuran (5 ml) was treated with 1M lithium aluminium hydride in tetrahydrofuran solution (1.1 ml, 1.1 mmol), and the resultant solution heated under reflux for 2 h. The solution was cooled, treated with dilute aqueous hydrochloric acid and extracted with ethyl acetate. The combined extracts were washed with brine, dried (sodium sulfate) and evaporated to give the title compound. MS (ESI) m/z: 435.1 [M+H]⁺.

EXAMPLE 46

3,5-Dimethyl-isoxazole-4-sulfonic acid 4-(5-fluoro-2-methoxy-pyridin-3-yl) benzylamide Di-tert-butyl dicarbonate (3.5 g, 16 mmol) and triethylamine (13 ml, 9.4 mmol) were added to a stirred solution of 4-aminomethylphenylboronic acid (3 g, 16 mmol) in tetrahydrofuran (100 ml). The reaction was stirred under reflux for 1 hour, then the solvent evaporated and the residue partitioned between water and ethyl acetate. The organic phase was concentrated under reduced pressure to give tert-butoxycarbonylaminomethyl-4-phenyl-boronic acid (2.67 g, 10.6 mmol) as a white solid. Toluene (16 ml), ethanol (4 ml), 2M sodium carbonate solution and tetrakis(triphenylphosphine) palladium (0) were added to tert-butoxycarbonylaminomethyl-4-phenyl-boronic acid (1.349 g, 5.4 mmol) and 3-bromo-5-fluoro-2-methoxy-pyridine (0.505 g, 2.45 mmol) and the mixture stirred under reflux for 24 h. Water was added and the mixture extracted with ethyl acetate. The organic phase was separated and the solvent evaporated. The residue was purified on silica gel eluting with 3:1 heptane/ethyl acetate to give [4-(5-fluoro-2-methoxy-pyridin-3-yl-benzyl]-carbamic acid-tert-butyl ester as a yellow oil. Trifluoroacetic acid (2 ml, 0.026 mmol) was added to a solution of [4-(5-fluoro-2-methoxy-pyridin-3-yl-benzyl]-carbamic acid-tert-butyl ester (0.8 g, 2.41 mmol) in dichloromethane (4 ml) and the reaction mixture stirred for 2 h. The solvent was evaporated and the residue partitioned between water and ethyl acetate. The organic phase was separated and the solvent evaporated to give 4-(5-fluoro-2-methoxy-pyridin-3-yl)-benzylamine. The title compound was prepared in a similar manner to N-[1-(2-allyl-5'-fluoro-2'-methoxy-biphenyl-4-yl)-ethyl]-3,4-difluoro-benzenesulfonamide (Example 34) using 4-(5-fluoro-2-methoxy-pyridin-3-yl)-benzylamine and 3,5-dimethyl-isoxazole-4-sulfonyl chloride. MS (ESI) m/z: 392 [M+H]⁺.

EXAMPLE 47

N-[4-(5-Cyano-2-methoxy-pyridin-3-yl)-benzyl]-2-trifluoromethoxy-benzenesulfonamide To a solution of 4-aminomethylphenylboronic acid hydrochloride (2.0 g, 13.2 mmol) in methanol (20 ml) was added di-tert-butyl dicarbonate (3.16 g, 15.5 mmol) and sodium bicarbonate (3.32 g, 19.8 mmol). The mixture was sonicated for 4 h then concentrated under reduced pressure. The residue was partitioned between ethyl acetate and water. The organic phase was washed with brine, dried over anhydrous magnesium sulfate and the solvent evaporated to give (4-bromo-benzyl)-carbamic acid tert-butyl ester (1.8 g, 13.2 mmol, 100%) as a white solid. To 6-chloro-nicotinonitrile (15 g, 0.11 mol) under argon atmosphere was added 25% sodium methoxide in methanol (11.7 g, 0.22 mol) and the mixture heated under reflux for 20 h. The methanol was evaporated and the residue partitioned between ethyl acetate and water. The aqueous phase was extracted with ethyl acetate. The combined organic extracts were washed with water, brine, dried over anhydrous magnesium sulfate and the solvent evaporated to give 6-methoxy-nicotinonitrile (17.0 g, 0.13 mol, 117%) as a white solid. To 6-methoxy-nicotinonitrile (13.2 g, 99 mmol) in acetic acid (32 ml) was added sodium acetate (8.1 g, 99 mmol). The mixture was stirred and a solution of bromine (31.5 g, 197 mmol) in acetic acid (32 ml) added. The mixture was heated to 80° C. for 48 h. The reaction mixture was poured into water and extracted with diethyl ether. The organic phase was washed with 4M aqueous sodium hydroxide solution, 5% sodium thiosulfate solution, dried over anhydrous potassium carbonate and the solvent was evaporated to give 5-bromo-6-methoxy-nicotinonitrile (11.9 g, 56 mmol, 57%). To a solution of 2-methoxy-5-cyanopyridine-3-boronic acid (1.0 g, 4.0 mmol) in 1,2-dimethoxyethane (10 ml) was added (4-bromo-benzyl)-carbamic acid tert-butyl ester (0.42 g, 2.0 mmol), tetrakis(triphenylphosphine)palladium (0) (114 mg, 0.1 mmol) and 2M aqueous sodium carbonate (1 ml, 2.0 mmol). The reaction was heated to 150° C. for 10 min in a microwave over. The mixture was concentrated under reduced pressure and partitioned between ethyl acetate and water. The organic phase was washed with water, then brine, dried over anhydrous magnesium sulfate and the solvent evaporated. The residue was purified on silica gel eluting with 5:1 heptane/ethyl acetate to give [4-(5-cyano-2-methoxy-pyridin-3-yl)-benzyl]-carbamic acid tert-butyl ester as a white solid (0.5 g, 1.47 mmol, 37%). To a solution of [4-(5-cyano-2-methoxy-pyridin-3-yl)-benzyl]-carbamic acid tert-butyl ester (0.5 g, 1.5 mmol) in dichloromethane (5 ml) at 0° C. was added trifluoroacetic acid (5 ml, 28 mmol). The reaction mixture was stirred for 30 min at 0° C. before the solvent was evaporated and the residue purified on a SCX column (eluted with 2M ammonia in methanol) to give 5-(4-aminomethyl-phenyl)-6-methoxy-nicotinonitrile as a clear glass (0.39 g, 1.6 mmol, 107%). To a solution of 5-(4-aminomethyl-phenyl)-6-methoxy-nicotinonitrile (57.3 mg, 0.24 mmol) in dichloromethane (2 ml) was added triethylamine (73.0 mg, 0.72 mmol) and 2-(trifluoromethoxy)benzenesulfonyl chloride. The reaction mixture was agitated for 20 hours and the solvent evaporated under reduced pressure. The crude product was taken up in dimethyl sulfoxide (1 ml) and purified by preparatory LCMS. The solvent was evaporated under reduced pressure to give the title compound (19.1 mg, 0.04 mmol, 17%). $^1$H NMR (400 MHz, DMSO-$d_6$): δ 8.68 (d, 1H), 8.47 (t, 1H), 8.15 (d, 1H), 7.90 (m, 1H), 7.73 (m, 1H), 7.45-7.55 (m, 4H), 7.31 (d, 2H), 4.19 (d, 2H), 3.96 (s, 3H) ppm; MS (ESI) m/z: 464.3 [M+H]$^+$.

EXAMPLE 48

1-Methyl-3-trifluoromethyl-1H-pyrazole-4-sulfonic acid [(S)-1-[4-(5-chloro-2-methoxy-pyridin-3-yl)-phenyl]-2-(4-methoxy-phenyl)-ethyl]-amide

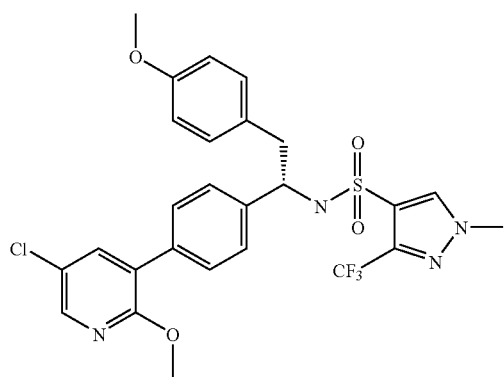

A solution of 2-Methyl-propane-2-sulfinic acid 1-[4-(5-chloro-2-methoxy-pyridin-3-yl)-phenyl]-methylideneamide (1 mmol) in THF (25 ml) at −78° C. was treated with 4-methoxybenzyl magnesium bromide (2 eq in THF). The reaction mixture was allowed to warm slowly to ambient temperature overnight. The reaction was quenched by the addition of saturated aqueous ammonium chloride (5 ml), extracted into ethyl acetate, dried (MgSO$_4$) and evaporated. The crude products were then purified by normal phase HPLC (SiO2; Ethyl.acetate). The fractions containing the desired product were pooled and evaporated. Deprotection with 4M HCl in dioxan followed by SCX purification (Strata™ 5 g/20 mLSCX column followed by elution with 2M ammonia in MeOH) yielded the free amine which was then treated with the required sulphonyl chloride (1.1 eq.) in dichloromethane containing DIEA (2 eq.). The reaction was then quenched by the addition of AcOH (500 L) and the desired product isolated by reverse phase HPLC (ZORBAX SB-C18 PrepHT 21.2×100 mm) eluting with a linear gradient of Acetonitrile/Water (0.1% TFA). The product containing fractions were then evaporated to yield the desire product as a clear glass. $^1$HNMR (DMSO-$d_6$)( , ppm):8.4 (d, 1H), 8.2 (s, 1H), 7.85 (s, 1H), 7.8 (s, 1H), 7.55 (d, 2H), 7.4 (d, 2H), 7.1 (d, 2H), 6.7 (d, 2H), 4.5 (m, 1H), 3.9 (s, 3H), 3.75 (s, 6H), 2.85 (d, 2H). MS(ESI): m/e 581.0 (M+1)$^+$

EXAMPLE 49

Glucocorticoid Receptor Binding Activity

The affinity of compounds was tested using a Glucocorticoid Receptor Competitor Assay kit (PanVera®). Components of the kit were thawed from −80° C. on ice (Fluormone GS1, recombinant human-GR (GR)) or at room temperature (GR screening buffer, stabilising peptide and DTT). 10 mM test compounds were manually diluted to 20 µM then serially diluted to a final concentration range of 10 µM to 0.1 nM using the BioMek 2000 (Beckman-Coulter) into a black walled 384 welled plate (Matrix technologies). In the following order: fluormone GS1 (1 nM final concentration) is added to all wells excluding the buffer control wells, GR (4 nM final concentration) is added to all wells except minimum and buffer control wells, cortisol (10 µM final concentration) is added to fluormone GS1 control wells only, buffer is added to all wells to a final volume of 40 µl. The plate is covered and incubated at room temperature with agitation for 90 minutes. Readings were taken using the Analyst (LJL) in fluorescence polarisation reading mode. The MilliP ratio is calculated from cps readings obtained in parallel and perpendicular mode. The percent effect of the bound ligand is calculated at each concentration and the dose response curves plotted allowing the $EC_{50}$ to be calculated. This is compared to the known standard ((11beta, 17beta)-11-(1,3-benzodioxol-5-yl)-17-hydroxy-17-(1-propynyl)estra-4,9-dien-3-one (CAS No. 189035-07-2), $EC_{50}=10^{-8}$ M). All compounds exemplified have binding activities <5×10$^{-8}$ M.

The invention claimed is:
1. A compound having the structure according to the formula I

Formula I

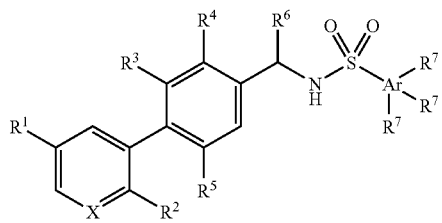

wherein:
X is a nitrogen atom;
Ar is 1H-pyrazole;
$R^1$ is hydrogen, halogen, CN or (1C-4C)alkyl;
$R^2$ is hydrogen, halogen or optionally fluorinated (1C-3C) alkoxy;
$R^3$ and $R^5$ are independently hydrogen, optionally halogenated (1C-4C)alkyl, optionally halogenated (1C-4C) alkoxy, optionally halogenated aryl(1C-4C)alkoxy, optionally halogenated (1C-4C)alkenyl or hydroxylmethyl;

R⁴ is hydrogen, halogen, optionally halogenated (1C-4C)alkoxy or optionally halogenated aryl(1C-4C)alkoxy;
R⁶ is optionally halogenated (1C-4C)alkyl; and
each R⁷ independently is hydrogen, halogen, optionally halogenated (1C-4C)alkyl or optionally halogenated (1C-4C)alkoxy;
or a pharmaceutically suitable acid addition salt thereof.

2. The compound according to claim 1, whereby:
R² is halogen or optionally fluorinated (1C-3C)alkoxy;
at least one of R³, R⁴ or R⁵ is hydrogen;
R⁶ is methyl;
or a pharmaceutically suitable addition salt thereof.

3. The compound according to claim 1, whereby
R¹ is hydrogen, halogen, CN or methyl;
R² is hydrogen, halogen or optionally fluorinated (1C-2C)alkoxy;
R³ and R⁵ are independently hydrogen, (1C-3C)alkyl, benzyloxy, (2C-3C)alkenyl, hydroxylmethyl or optionally fluorinated methoxy;
R⁴ is hydrogen, F, Cl or methoxy and at least one of R³, R⁴ and R⁵ is hydrogen;
R⁶ is methyl;
each R⁷ independently is hydrogen, optionally fluorinated methyl, optionally fluorinated methoxy, F, Cl or Br;
or a pharmaceutically suitable addition salt thereof.

4. The compound according to claim 1, wherein the compound is N-[(1R)-1-(5-chloro-2-methoxy-3-pyridinyl)phenyl]ethyl-1-methyl-3-(trifluoromethyl)-1H-pyrazole-4-sulfonamide or a pharmaceutically suitable addition salt thereof.

5. A pharmaceutical composition comprising the compound according to claim 1 or a pharmaceutically suitable addition salt thereof and a pharmaceutically acceptable excipient.

6. A pharmaceutical composition comprising the compound according to claim 4 or a pharmaceutically suitable addition salt thereof and a pharmaceutically acceptable excipient.

* * * * *